United States Patent
Dewaele et al.

(12)

(10) Patent No.: US 11,832,997 B2
(45) Date of Patent: Dec. 5, 2023

(54) DEVICES TO ENHANCE ROBOTIC ARM TASKS

(71) Applicant: Steerable Instruments NV, Sint-Denijs-Westrem (BE)

(72) Inventors: Frank Dewaele, De Pinte (BE); Lieven Maene, Knokke-Heist (BE); Bart Blanckaert, Eeklo (BE); Cyriel Mabilde, Oudenaarde (BE); Alain Kalmar, Ghent (BE)

(73) Assignee: Steerable Instruments NV, Sint-Denijs-Westrem (BE)

( * ) Notice: Subject to any disclaimer, the term of this patent is extended or adjusted under 35 U.S.C. 154(b) by 492 days.

(21) Appl. No.: 16/763,396

(22) PCT Filed: Nov. 15, 2018

(86) PCT No.: PCT/EP2018/081438
§ 371 (c)(1),
(2) Date: May 12, 2020

(87) PCT Pub. No.: WO2019/096933
PCT Pub. Date: May 23, 2019

(65) Prior Publication Data
US 2020/0315738 A1 Oct. 8, 2020

(30) Foreign Application Priority Data

Nov. 15, 2017 (EP) ..................................... 17201821

(51) Int. Cl.
*A61B 90/50* (2016.01)
*A61B 34/37* (2016.01)
(Continued)

(52) U.S. Cl.
CPC .............. *A61B 90/50* (2016.02); *A61B 34/37* (2016.02); *A61B 90/35* (2016.02); *A61M 13/003* (2013.01);
(Continued)

(58) Field of Classification Search
CPC ......... B25J 9/0018; A61B 90/35; A61B 90/50
See application file for complete search history.

(56) References Cited

U.S. PATENT DOCUMENTS 5,184,601 A 2/1993 Putman
10,016,900 B1 * 7/2018 Meyer .................... G05B 19/00
(Continued)

FOREIGN PATENT DOCUMENTS

ES 2206038 A1 5/2004
WO WO-2004028754 A1 * 4/2004 .............. B25J 5/007

OTHER PUBLICATIONS

International Search Report dated Jun. 14, 2019 from PCT International Patent Application No. PCT/EP2018/081438.
(Continued)

*Primary Examiner* — Randell J Krug
(74) *Attorney, Agent, or Firm* — Amster, Rothstein & Ebenstein LLP

(57) ABSTRACT

Provided is a stable mounting for a robotic arm, a tool changer for a robotic arm, a motion restrictor for a robotic-arm controlled steerable tool, a dispenser unit for applying a sterile drape over a robotic arm, and a tool radial actuation assembly (TRAA), a robotic arm fitting radial actuation assembly (FRAA).

14 Claims, 20 Drawing Sheets

(51) Int. Cl.
    *A61B 90/35*    (2016.01)
    *A61M 13/00*    (2006.01)
    *A61B 1/00*    (2006.01)
    *A61B 6/00*    (2006.01)
    *A61B 8/00*    (2006.01)
    *A61B 17/3201*    (2006.01)
    *A61B 17/3209*    (2006.01)
    *A61B 17/34*    (2006.01)
    *A61B 18/14*    (2006.01)
    *A61B 17/00*    (2006.01)
    *A61B 18/00*    (2006.01)
    *A61M 25/01*    (2006.01)

(52) U.S. Cl.
    CPC ......... *A61B 1/00158* (2013.01); *A61B 6/4441* (2013.01); *A61B 8/4444* (2013.01); *A61B 17/3201* (2013.01); *A61B 17/3209* (2013.01); *A61B 17/3474* (2013.01); *A61B 18/14* (2013.01); *A61B 2017/00991* (2013.01); *A61B 2018/00589* (2013.01); *A61B 2217/005* (2013.01); *A61M 25/0116* (2013.01)

(56) References Cited

U.S. PATENT DOCUMENTS

| | | |
|---|---|---|
| 2004/0243147 A1 | 12/2004 | Lipow |
| 2007/0250113 A1 | 10/2007 | Hegeman et al. |
| 2010/0286669 A1 | 11/2010 | Greer et al. |
| 2012/0289974 A1 | 11/2012 | Rogers et al. |
| 2014/0005704 A1 | 1/2014 | Vakharia et al. |
| 2015/0148818 A1 | 5/2015 | Lohmeier et al. |
| 2015/0164596 A1 | 6/2015 | Romo et al. |

OTHER PUBLICATIONS

Written Opinion dated Jun. 14, 2019 from PCT International Patent Application No. PCT/EP2018/081438.

* cited by examiner

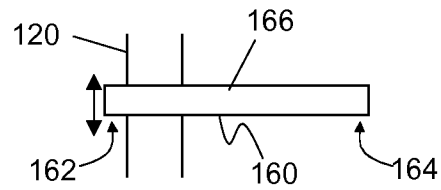
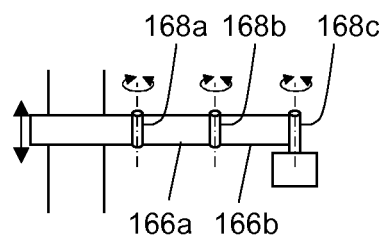
FIG. 4  FIG. 5
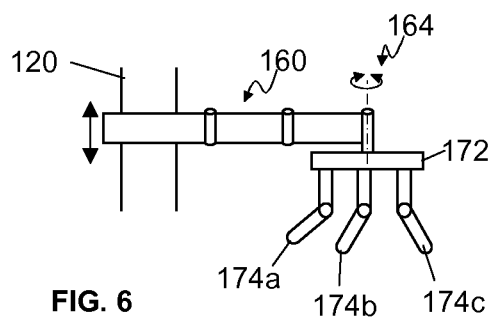
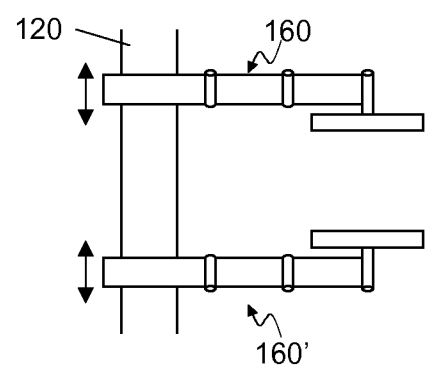
FIG. 6  FIG. 7
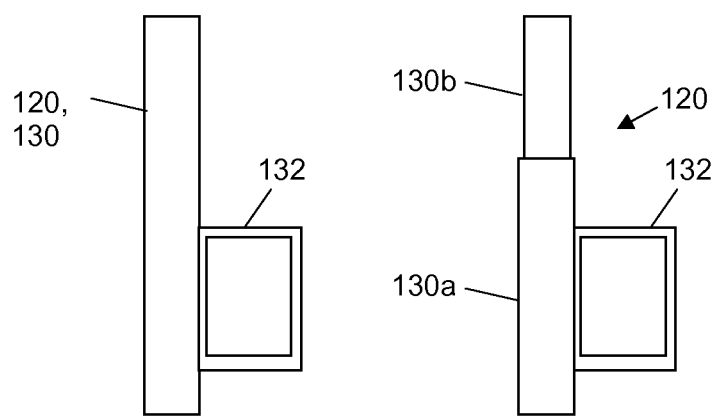
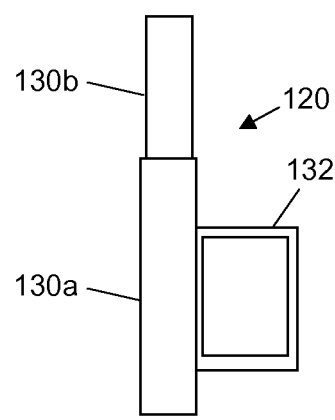
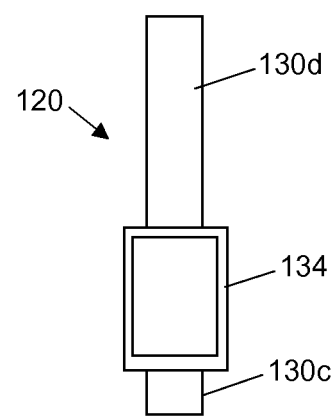
FIG. 8  FIG. 9  FIG. 10

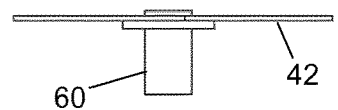
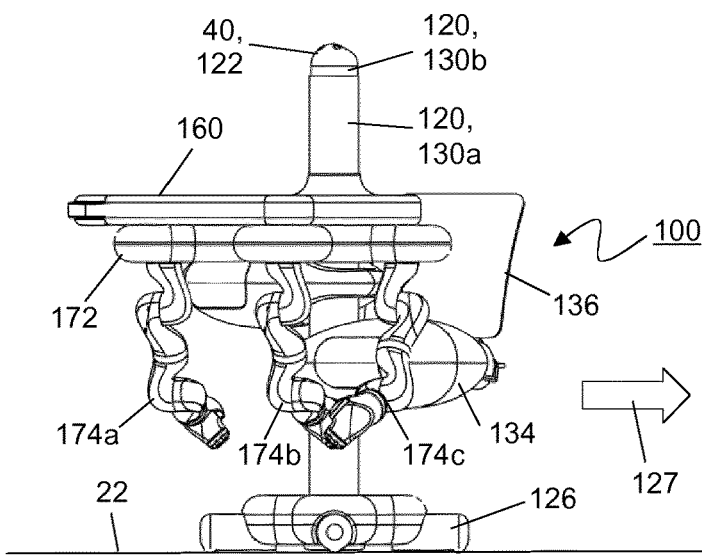
FIG. 11A
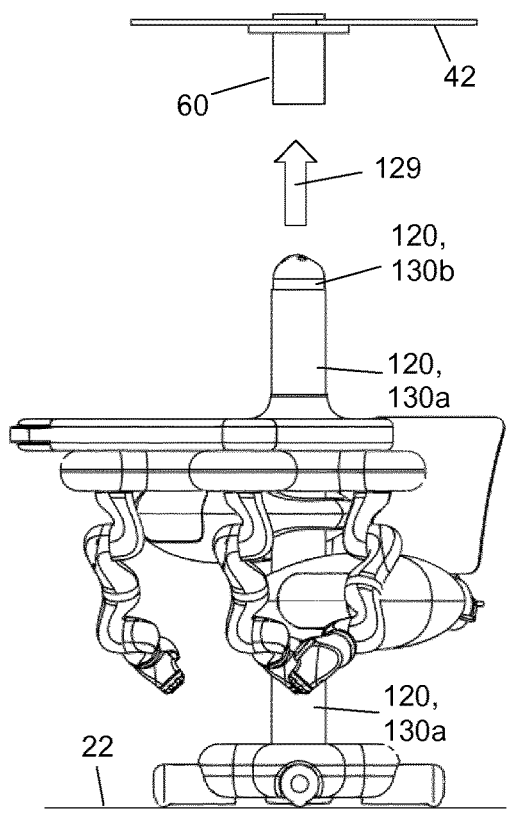
FIG. 11B
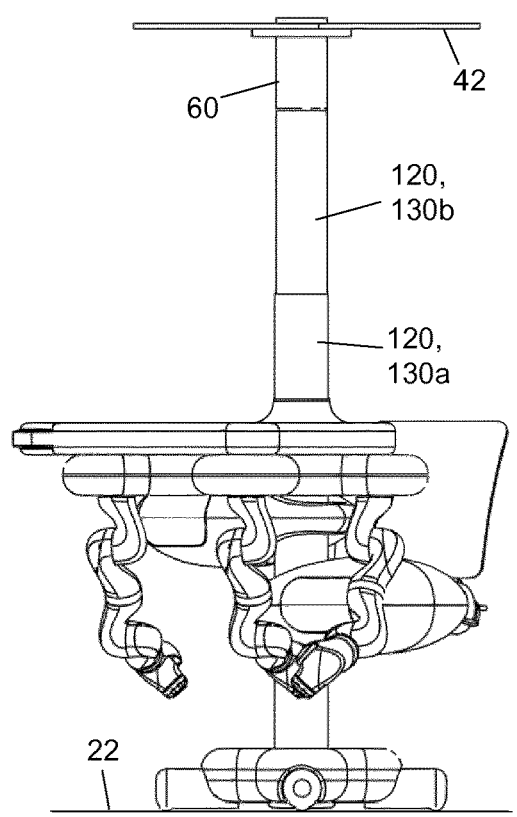
FIG. 11C

FIGs. 26 to 28: Blank

Figure 44:
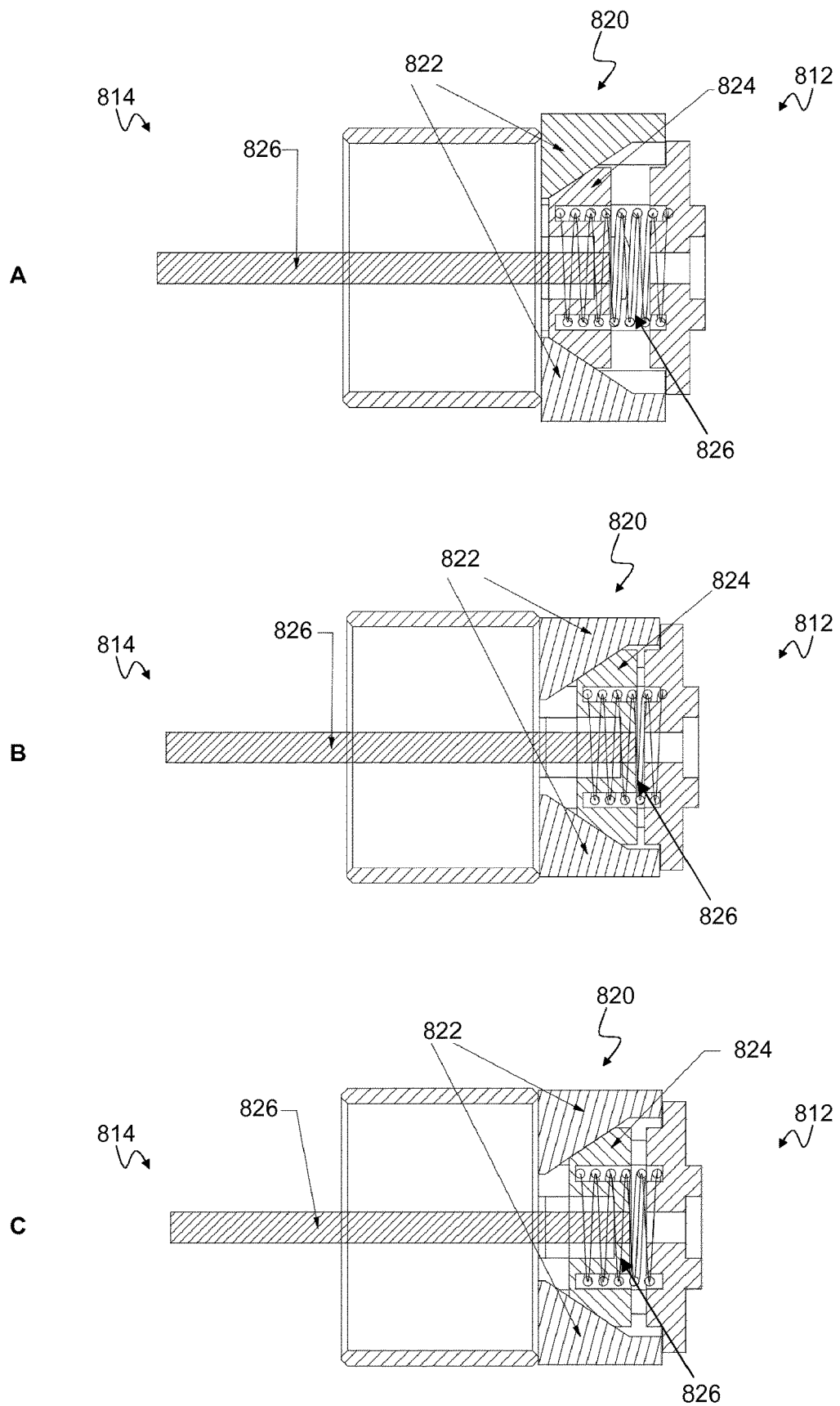

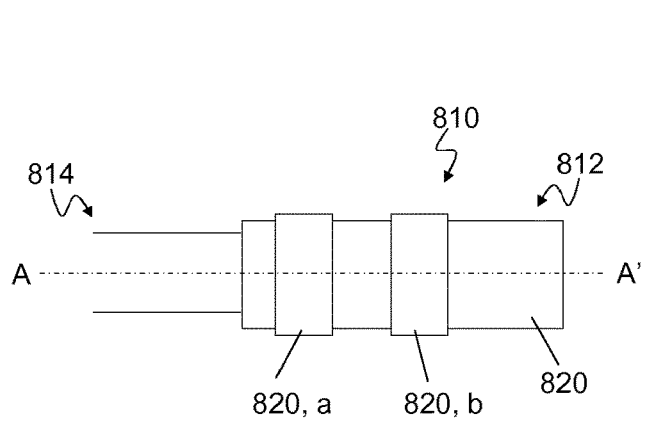
FIG. 40
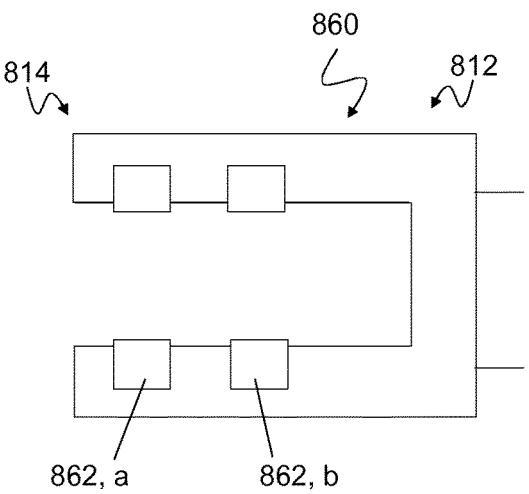
FIG. 41
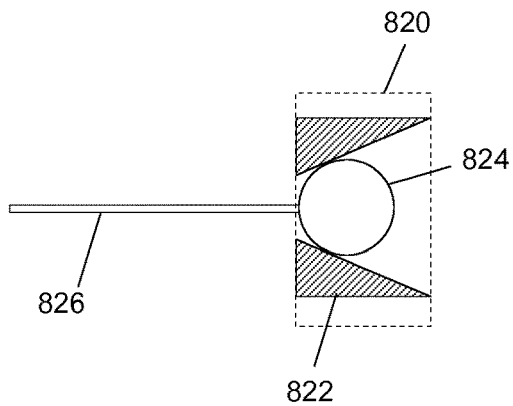
FIG. 42A
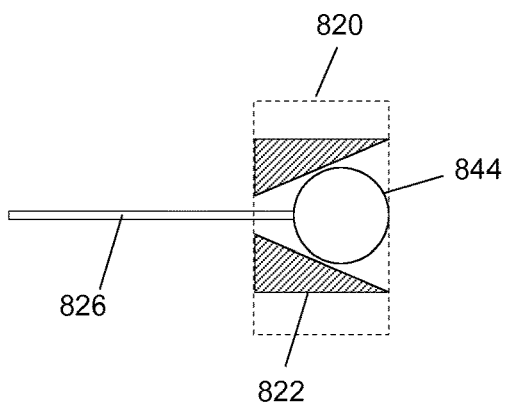
FIG. 42B
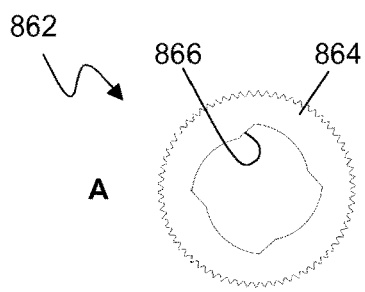
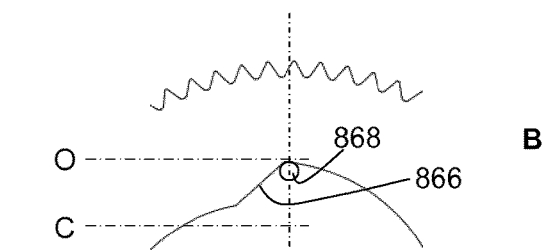
FIG. 43
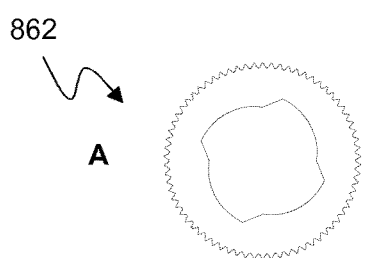
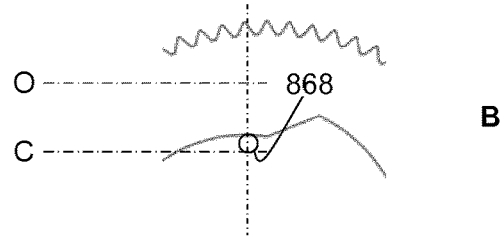
FIG. 44

DEVICES TO ENHANCE ROBOTIC ARM TASKS

CROSS-REFERENCE TO RELATED APPLICATIONS

This application is a U.S. national stage entry under 35 U.S.C. § 371 of PCT International Patent Application No. PCT/EP2018/081438, filed Nov. 15, 2018, which claims priority to European Patent Application No. 17201821.0, filed Nov. 15, 2017, the contents of each of which are incorporated herein by reference in their entirety.

FIELD OF THE INVENTION

Stable mounting for a robotic arm, tool changer for a robotic arm, straightening element for a robotic-arm controlled steerable tool, and a dispenser unit for applying a sterile drape over a robotic arm.

SUMMARY

Provided is a structural support unit, SSU, (100) for vertical fitting in a room and for support of a boom unit (160) comprising:
  a telescopic vertical supporting part, VSP, (120) having an lower end (20) and an upper end (40), the lower end (20) configured for contacting a floor (22) of the room (10) and an upper end (40) configured for attachment to a VSP receivable mounting (60) in the ceiling (42) of the room (10) thereby stabilising the structural support unit (110) in relation to the room for support of the boom unit (160)
  the boom unit (160) that is slidably and optionally revolutely attached to at least part of the VSP (120), wherein
  a load of the boom unit (160) comprises an assembly of two or more surgical robotic arms (174a-c),
  the VSP (120) comprises a telescopic part (130), configured to retract and deploy the upper end (40) of the VSP (120).

Provided is also a structural support unit, SSU, (100) for vertical fitting in a room and for support of a boom unit (160) comprising:
  a vertical supporting part, VSP, (120) having an lower end (20) and an upper end (40), the lower end (20) configured for contacting a floor (22) of the room (10) and an upper end (40) configured for contacting a ceiling (42) of the room (10) thereby stabilising the structural support unit (110) in relation to the room for support of the boom unit (160).

The structural support unit (100) may be provided, wherein:
  the base end (20) of the VSP (120) is configured for non-adjustable attachment to the floor (22) and/or the upper end (40) of the VSP (120) is configured for non-adjustable attachment to the ceiling, or
  the base end (20) of the VSP (120) is configured for adjustable attachment to the floor (22) and/or the upper end (40) of the VSP (120) is configured for adjustable attachment to the ceiling.

The structural support unit (100) may be provided wherein:
  the base end (20) of the VSP (120) is disposed with a steerable dolly (126) configured to support and transport the VSP (120), and a
  the VSP (120) comprises a telescopic part (130), configured to retract and deploy the upper end (40) of the VSP (120)
configured to provide portability to the structural support unit (100).

The structural support unit (100) may be provided wherein the boom unit (160) is slidably attached to at least part of the VSP (120).

The structural support unit (100) may be provided wherein the VSP (120) comprises
  a load-bearing cylindrical tube (130), or
  a telescopic load-bearing cylindrical tube (130a, b), or
  a combination of one or more non-telescopic (130c, d) load-bearing cylindrical tubes and a load bearing storage unit (134).

The structural support unit (100) may be provided wherein the boom unit (160) has a proximal end (162) attached to the VSP (120) and a distal end (164) attached to a load.

The structural support unit (100) may be provided wherein the load of the boom unit (160) comprises an assembly of one or more robotic arms (174a-c).

The structural support unit (100) may be provided wherein the VSP (120) is disposed with one or more further boom units (160').

The structural support unit (100) may be provided wherein cables and tubing are disposed within void spaces of the VSP (120) and/or boom unit (160) and/or further boom unit (160')

The structural support unit (100) may be provided configured for use in an operating theatre, wherein
  the load of the boom unit (160) is an assembly of one or more surgical robotic arms (174a-c)
  the VSP (120) comprises a combination of a telescopic or non-telescopic load-bearing cylindrical tube and a load bearing or no-load-bearing storage unit configured to store one or more of:
    a surgeon console for manual operation of the one or more surgical robotic arms,
    light source,
    high frequency coagulator,
    insufflator.

Also provided is a use of a structural support unit (100) as described herein in an operating the theatre comprising attaching the VSP upper end (40) to the VSP receivable mounting (60) placed in the ceiling of the operating theatre.

Further provided is a system (200) comprising:
  a robotic arm, RA, (220) having a base end (222) and an effector end (224) disposed with a RA fitting (226) for repeatable dismountable attachment to a tool (242a-c) for working on an object (210),
  the robotic arm (220) configured to control a position and/or direction of the tool (242a-c) for working on the object,
  the robotic arm (220) further configured to:
    direct the RA fitting (226) to a tool storage unit (240) holding a plurality of tools (242a-c) for working on the object (210)
    effect attachment of a selected tool (242a) from the plurality of tools (242a-c) in the tool storage unit (240) to the RA fitting (226) for working on the object (210),
    effect return to the tool storage unit (240) of the selected tool (242a) to its location, and detachment from the RA fitting (226).

The system may be provided wherein the robotic arm (220) is a surgical robotic arm, and the tool (242a-c) is a surgical instrument, selected from:
- standard surgical instrument—knife, scissors, suction tube, trocar, Verass needle,
- ultra sound probe
- steerable surgical instrument
- c-arm
- controller for a magnetic intracorporeal camera
- catheter
- HF coagulator tool, wherein the RA fitting is provided with a coupling for supply of signals and power to the HF coagulator tool The system may be provided wherein the tool storage unit (240) is configured to receive a tool (242a-c) provided in a sterile packaging.

The system may be provided wherein the RA fitting (226) repeatable dismountably attaches to a tool (242a-c) using a motorised connector, a spring-loaded connector, a manually-activated connector (e.g. screw, latch, bolt, bar)

The system may be provided wherein the tool storage unit (240) comprises a moveable selector (e.g. carousel) configured to offer a selected tool from the plurality of tools for attachment to the RA fitting.

The system may be provided wherein the tool storage unit (240) comprises a plurality of fixed-position locators (244a-c) one for each of the plurality of tools (242a-c).

The system may be provided comprising one or more further robotic arms, (220') wherein the tool connector (246a, 410) and respective RA fittings (226, 226') are configured for a transfer of the tool (242a) from the robot arm (220) to one of the further robotic arms (220').

The system may be provided disposed with a position sensing device (e.g. camera) and controller configured to determine from the position sensing device a position of a distal end of the tool (242a-c) for automated docking of the distal end of the tool (242a-c) into a working space.

The tool (442) may be a tool that is steerable and controllable by the robotic arm, having a proximal end (404) and a distal (406) end, said tool comprising:
- a shaft (430), a bendable proximal part (420) and a bendable distal part (440),
- a tool connector (410) configured for dismountable attachment to the robotic arm, attached in fixed rotational relation to the bendable proximal part (420),
- an end effector (450) attached in fixed rotational relation to the bendable distal part (440),
- the tool (402) configured such that:
- the bendable distal part (440) bends responsive to bending of the bendable proximal part (420), and the end effector (450) is rotatable when the bendable distal part (440) is in a bent position by a complementary rotation of the connector (410), thereby providing control of the shaft (430) direction, bending of the bendable distal part (440), and rotation of the end effector (450) through robotic movement of the connector (410)

and the RA fitting (226) is configured for dismountable attachment to the connector (410) of the steerable tool.

Further provided is a tool package for use with the system (200) herein, comprising
- a sterile packaging
- a tool (242a-c) deposed in the sterile packaging,
wherein:
the sterile packaging is configured for dismountable attachment to the tool-storage unit (240), and the tool is repeatable dismountably attached to the sterile packaging.

Further provided is tool package for use with the system (200) comprising
- a sterile packaging
- a tool (242a-c) deposed in the sterile packaging,
wherein
the sterile packaging is configured for dismountable attachment to the tool-storage unit (240), and
the tool is repeatable dismountably attached to the sterile packaging and the tool (442) is steerable and controllable as defined herein.

Further provided is a tool assembly (400) comprising a tool (402) that is steerable and controllable by a robotic arm, having a proximal end (404) and a distal (406) end comprising:
- a shaft (430), a bendable proximal part (420) and a bendable distal part (440),
- a connector (410) configured for dismountable attachment to the robotic arm, attached in fixed rotational relation to the bendable proximal part (420),
- an end effector (450) attached in fixed rotational relation to the bendable distal part (440),
- the tool (402) configured such that:
- the bendable distal part (440) bends responsive to bending of the bendable proximal part (420), and the end effector (450) is rotatable when the bendable distal part (440) is in a bent position by a complementary rotation of the connector (410), thereby providing control of the shaft (430) direction, bending of the bendable distal part (440), and rotation of the end effector (450) through robotic movement of the connector (410), further comprising a deployable motion restrictor (460), configured to restrict bending of and optionally straighten the bendable proximal part (420) after deployment.

The motion restrictor (460) may be configured to span the bendable proximal part (420) and at least part of the connector (410) when deployed, and to clear the bendable proximal part (420) when retracted. The tool assembly (400) may be provided wherein the motion restrictor (460) comprises a rigid member disposed in slidable relation to the connector (410) configured to span the bendable proximal part (420) and at least part of the connector (410) when deployed. The tool assembly (400) may be provided wherein the rigid member comprises a rigid sleeve, slidable in a distal direction for deployment, and retractable in a proximal direction to release the bendable proximal part (120) for bending. The tool assembly (400) may be provided wherein the fitting comprises a slidable coupling configured to couple with the motion restrictor (460), and for deployment and retraction of the motion restrictor.

Further provided is a dispenser unit (600) for applying a sterile drape (620) over a surgical robotic arm (174a/650) having a base end (652) and an effector end (654) comprising:
- a sterile drape (620) with longitudinal sleeve form (622) closed at one end (624) and open at the other (626), folded so as to reduce its longitudinal length while maintaining a passage (628) through the folded sleeve (622) to the closed end (624),
- an applicator (660) fixed, optionally detachably, to the open end (626) of the longitudinal sleeve (622),
wherein
the passage (628) is configured to receive the robot arm (174a/650), the closed end (624) of the longitudinal sleeve (622) is configured to abut with robot arm effector end (656), the dispenser unit (600) configured to unfold the longitudinal sleeve (622) over the robotic arm (650) by movement of the applicator (660) or robotic arm (174a/650) to bring the applicator (660) closer to the base end (652) of the robotic arm (174a/650).

The dispenser unit (600) may be provided comprising a plurality of applicators (660a-d) and sterile drapes (620a-d), each applicator (660a-d) being attached to one or more other applicators (660a-d) in the dispenser unit (600). The dispenser unit (600) may be provided wherein the applicator (660, 660a-d) is disposed with a coupling (632) for dismountable attachment to a support (632) configured to maintain the applicator (660, 660a-d) in a fixed position relative to the robotic arm (174a/650) while the robotic arm (174a/650) advances into the passage (628) thereby bringing the applicator (660, 660a-d) closer to the base end (652) of the robotic arm (174a/650). The dispenser unit (600) may be provided wherein the open end (626) of the longitudinal sleeve (620) is provided with one or more magnetic clasps, configured for dismountable attachment to the robotic arm (174a/650).

Further provided is a tool (810) for attachment to a fitting (860) of a robotic arm, the tool (810) having a proximal (812) and distal (814) end, the proximal (812) end is dismountably attachable to the robotic arm fitting (860) via a tool connector (820), wherein the tool (810) is provided with one or more slidable actuateable elements (826), SAE, the tool connector (820) is provided with one or more tool radial actuation assemblies, TRAA, (820) configured to a receive a radial force, provided by a fitting (860) on the robotic arm and to transform it to a longitudinal force for actuation of the SAE (826). The tool (810) may be provided wherein the TRAA (820) comprises one or more wedge-shaped bodies (822) radially slidable with respect to a central axis (A-A') of the connector (820) and is in contact with a longitudinally slidable body (824), wherein radial movement of the wedge-shape body (822) induces a longitudinal displacement of the longitudinally slidable body (824). The tool (810) may be provided with a plurality of wedge-shaped bodies (822), arranged to form an annulus shape. The tool (810) may be provided wherein the longitudinally slidable body (824) is disposed in relation to a compliant member (826) configured to bias the longitudinally slidable body (824) in a neutral position when no external force is applied to the wedge shape body (822).

Further provided is a fitting (860) for an effector end of the robotic arm provided with a fitting radial actuation assembly (FRAA) (862) configured to engage with the connector (820) of a tool (810) described herein and provide a radial force for actuation of the TRAA (820). The fitting (860) may be provided wherein the FRAA (862) comprises a rotatable member (864) disposed with a cammed or eccentric surface (886), whereby rotation of the rotatable member (864) causes displacement of a slider (868) which slider provides a radial force for actuation of the TRAA (820). The fitting (860) may be provided wherein the slider (868) is configured to slide in a radial direction only.

DETAILED DESCRIPTION OF INVENTION

Before the present devices, systems and methods are described, it is to be understood that this invention is not limited to particular devices, systems and methods or combinations described, since such devices, systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal" and "proximal" are used through the specification, and are terms generally understood in the field to mean towards (proximal) or away (distal) from the user or surgeon's side of the apparatus. Thus, "proximal" means towards the user or surgeon's side and, therefore, away from the working side or patient's side. Conversely, "distal" means towards the working side or patient's side and, therefore, away from the user or surgeon's side.

The present invention provide according to a first aspect, structural support unit, SSU (see e.g. FIGS. 1 to 12C)

The structural support unit, SSU (100) for vertical fitting in a room (10) and for support of a (horizontal) (load-bearing) boom unit (160) comprising:

a vertical supporting part (VSP) (120) having an lower end (20) and an upper end (40), the lower end configured for contacting a floor (22) of the room and an upper end configured for contacting a ceiling (42) of the room thereby stabilising the structural support unit (100) in relation to the room for support of the boom unit.

By having points of contact with the floor (22) and ceiling (42) within a room, the boom unit (160) is supported more stably, in particular for a system that requires fine and fast movements. There is also less foot print, since no weight base is required. There is also improved cable management. It is noted that the ceiling (42) refers to a structural load-bearing ceiling, and not to a false ceiling.

The boom unit (160) may disposed essentially horizontally with respect to the vertical supporting part (VSP) (120)

Figure 1:
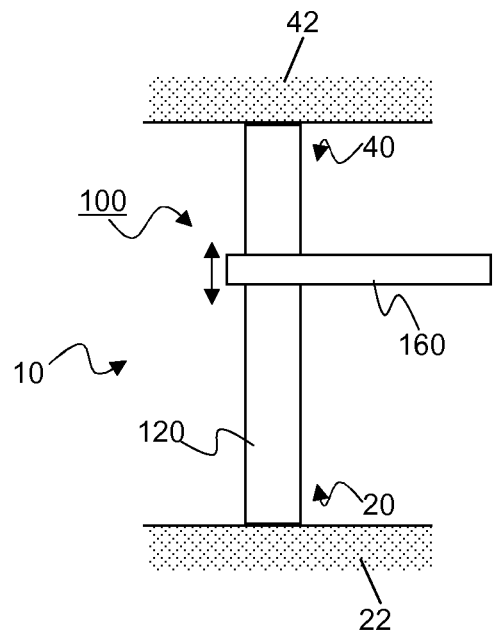

The base end (20) of the vertical supporting part (120) may be configured for non-adjustable attachment to the floor (22) (see, e.g. FIG. 1). By non-adjustable, it is meant it is fixed to the floor for a service life of the SSU. The upper end (40) of the vertical supporting part (120) may be configured for non-adjustable attachment to the ceiling (42) (see, e.g. FIG. 1). By non-adjustable, it is meant it is fixed to the ceiling for a service life of the SSU. The upper end (40) of the vertical supporting part (120) may be configured for adjustable attachment to the ceiling (42) (see later below).

Cables and tubing may be disposed within void spaces of the SSU and/or boom unit and/or further boom unit. Cables, either continuous of via connector may further run through the SSU into the space between the structural ceiling and the false ceiling. It reduces the time required for sterile cleansing and/or cleaning when the SSU is used in an operating theatre.

Figure 2:
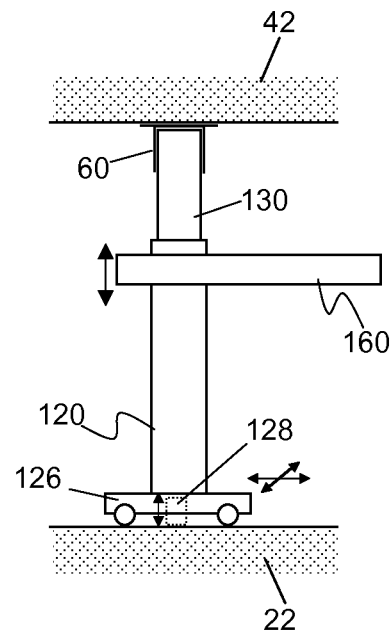
Figure 3:
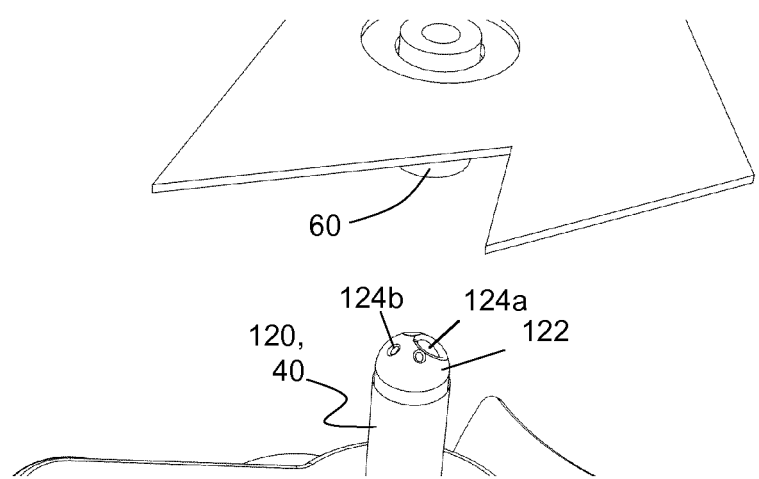

The base end (20) of the vertical supporting part (120) may be disposed with a steerable dolly (126) configured to support and transport the vertical supporting part (120) (see, e.g. FIG. 2). The steerable dolly is configured to provide portability to the structural support unit (100). A steerable dolly (126) is typically a low-centre of gravity moveable platform configured to support and move large loads. The dolly (126) may be motorised. A steerable handle or control may be provided. The dolly (126) may be disposed with a deployable foot (128) to raise the dolly from the wheels during use. Weight of the SSU (110) and any loads are supported by the deployable foot (128). The dolly may be disposed with retractable wheels to lower the dolly onto its base during use; the weight of the SSU (110) and any loads are supported by the dolly base (128). The dolly may be provided with spreadable wheels in order to increase the footprint of the dolly to maintain the SSU upright in a stable and safe way during transport.

The VSP (120) may comprise a load-bearing cylindrical tube (130) (see, for instance, FIG. 8). A (non-load bearing) storage unit (132) may be attached to the load-bearing cylindrical tube (130). The VSP (120) may comprise a telescopic load-bearing cylindrical tube (130) (see, for instance, FIG. 9). The telescopic load-bearing cylindrical tube (130) may comprise a base load-bearing cylindrical tube (130a) and an extendible load-bearing cylindrical tube (130b) in slidable relation to the base load-bearing cylindrical tube (130a). A (non-load bearing) storage unit (132) may be attached to the base load-bearing cylindrical tube (130a). The VSP (120) may comprise a combination of one or more load-bearing cylindrical tubes (130c,d) and a load bearing (vertical) storage unit (134) (see, for instance, FIG. 10). The load bearing storage unit may comprise one or a plurality of load bearing storage compartment joined together. The load bearing storage unit may be vertically arranged. The storage unit (132, 134) may be configured to store equipment, controllers, and the like. Wherein the SSU (110) is used in an operating theatre and is disposed with one or more robotic arms, the storage unit (132, 134) may be configured to store one or more of:

a surgeon console for manual operation of the one or more surgical robotic arms,
light source,
high frequency coagulator,
insufflator.

The vertical supporting part (120) may comprise a telescopic part (130), configured to retract and deploy the upper end (40) of the VSP (120). The telescopic part may be motorised, hydraulically operated, pneumatically operated. It may comprise one or more extendible parts. The telescopic part (130) assists with the portability of the SSU (100). The telescopic part (130), allows the VSP (120) to be lowered for transport of the SSU (100) between rooms, in particular through a door that has a lower height clearance. The telescopic part (130) allows the VSP (120) to be raised for use so that it contacts the ceiling (42). The telescopic part (130), may retract the VSP to ~2 m to allow transport of the SSU on the dolly through a door. The telescopic part (130), may extend the VSP to ~3 m to allow securing contact with a ceiling (42) of a room (10).

An unexpected advantage of a telescopic part (130) is that parasite vibrations from the ceiling i.e. an upper floor are not transmitted to the actuator (scissor or grasper) as the upper part of the VSP can dock into a VSP receivable mounting (60) attached to the ceiling (42) of the room (10), without relying on pressure to hold the VSP in position. Hence, the VSP is not held in place by tension; VSP receivable mounting (60) prevents the VSP from tilting, hence vibrations are not transmitted through the VSP that can affecte surgical procedures. Parasite vibrations from the floor are not an issue since operating table and VSP receive the same. Another Advantage is a smaller foot print.

A VSP receivable mounting (60) (see, e.g. FIGS. 2 and 3) may be provided for attachment to the ceiling (42) of the room (10). It is configured to mechanically couple with the VSP upper end (40). The mechanical coupling may be dismountable. The VSP receivable mounting (60) may configured for repeatable dismountable coupling with the VSP upper end (40). VSP receivable mounting (60) in particular receives a telescopic VSP upper end (40); the telescopic part (130) may be raised for use so that it couples with the VSP receivable mounting (60).

The VSP receivable mounting (60) may be non-adjustably attached to the ceiling; by non-adjustable, it is meant it is fixed to the ceiling for a service life of the SSU (100) or of the VSP receivable mounting (60). The VSP receivable mounting (60) may be adjustably attached to the ceiling; it allows the position of the SSU (100) within the room to be adjusted. The VSP receivable mounting (60) may be attached to the ceiling on a slidable rail. The VSP receivable mounting (60) may be attached to the ceiling on a swing-arm assembly. The swing arm assembly may comprise one or more arms of a kinematic chain connected by revolute and/or prismatic joints. The VSP receivable mounting (60) may be vertically slidably deployable and retractable (e.g. to a distance of ~1 m)

The VSP receivable mounting (60) may be disposed with one or more service connectors for supply of services (e.g. electricity, water, gas, data) to the SSU (100). The VSP (120) upper end (40) may terminate in a hub (122) (see e.g. FIG. 3) is disposed with one or more reciprocating service connectors (124a, 124b) for connecting to the service connectors of the VSP receivable mounting (60). A safety feature may be present that that checks adequate docking of the VSP upper end (40) to the VSP receivable mounting (60) before the boom unit (160) is deployed.

The VSP receivable mounting (60) may comprise a slot, preferably having a circular profile, into which the VSP upper end (40) engages. The slot stabilises the VSP (120) in a vertical direction; when a load is placed on the boom unit (160) it prevents the VSP (120) from being destabilised and tilting. In particular, the slot in the VSP-receivable mounting avoids the need to introduce tensile compression forces to the walls and ceiling and hence the service connectors do not require adaptation to withstand compression forces. Coupling avoids the use of force which extends the life span of a repeatable coupling, particularly important for fluid lines such as compressed air and water.

The boom unit (160) may be slidably, and optionally revolutely attached to at least part of the VSP (120) (see for instance, FIGS. 4 to 7). Slidable attachment allows controlled movement of the boom unit (160) along a vertical/axial length of the VSP (120). The boom unit (160) has a proximal end (162) (rotationally) attached to the VSP (120) and a distal end (142) (rotationally) attachable to a load (see FIG. 4). The boom unit (160) at the proximal end (162) may be disposed in rotational relation with the VSP (120) (see. FIG. 5)

The boom unit (160) may comprise one arm (166), or two or more arms (166a, b) of a kinematic chain in mutual connection by revolute (168a-c) and/or prismatic joints (FIG. 5).

Providing a plurality of arms (166a, b) allows adjustment of the position of the load in three degrees of freedom. It may also assist with storage of the SSU (100); by bringing the load closer to the VSP (120) when not in use, the SSU (100) occupies less space. Further, where the SSU (100) is transportable, it brings a centre of gravity of the SSU (100) towards the VSP (120).

The load of the boom unit (160) may comprise a C-arm, a microscope or any other heavy device or any other device that requires stable support and which is moveable.

The load of the boom unit (160) may comprise an assembly of one or more robotic arms (174 a-c), (see for instance FIG. 6). At least two robot arms (174 a-c) may be provided, attached at their base ends to a support (172), the support (172) attached to the distal end (164) of the boom unit (160). The support may be rotatably or revolutely attached to the boom unit (160). Each robotic arm have 6 or 7 or more degrees of freedom of movement of an effector end. The number of robotic arms may be two, three or more. One or more of, preferably each and every robotic arm in the assembly may be a surgical robotic arm.

The VSP is disposed with one or more further boom units (160') (see for instance FIG. 7). The load of a further boom unit (160') may be an operating table.

The SSU (100) is preferably configured for use in an operating theatre. The load of the boom unit (160) may be an assembly of one or more surgical robotic arms (174-a-c). The VSP (120) may comprise a combination of a telescopic or non-telescopic load-bearing cylindrical tube and a load-bearing (134) or non-load bearing (132) storage unit configured to store one or more of:

a surgeon console for manual operation of the one or more surgical robotic arms,
a screen/monitor
light source,
high frequency coagulator,
insufflator.

Also provided is use of an SSU in an operating the theatre comprising attaching the VSP upper end (40) to a VSP receivable mounting (60) placed in the ceiling of the operating theatre. The attaching may be dismountable. The attaching may be repeatable and dismountable.

Figure 13:
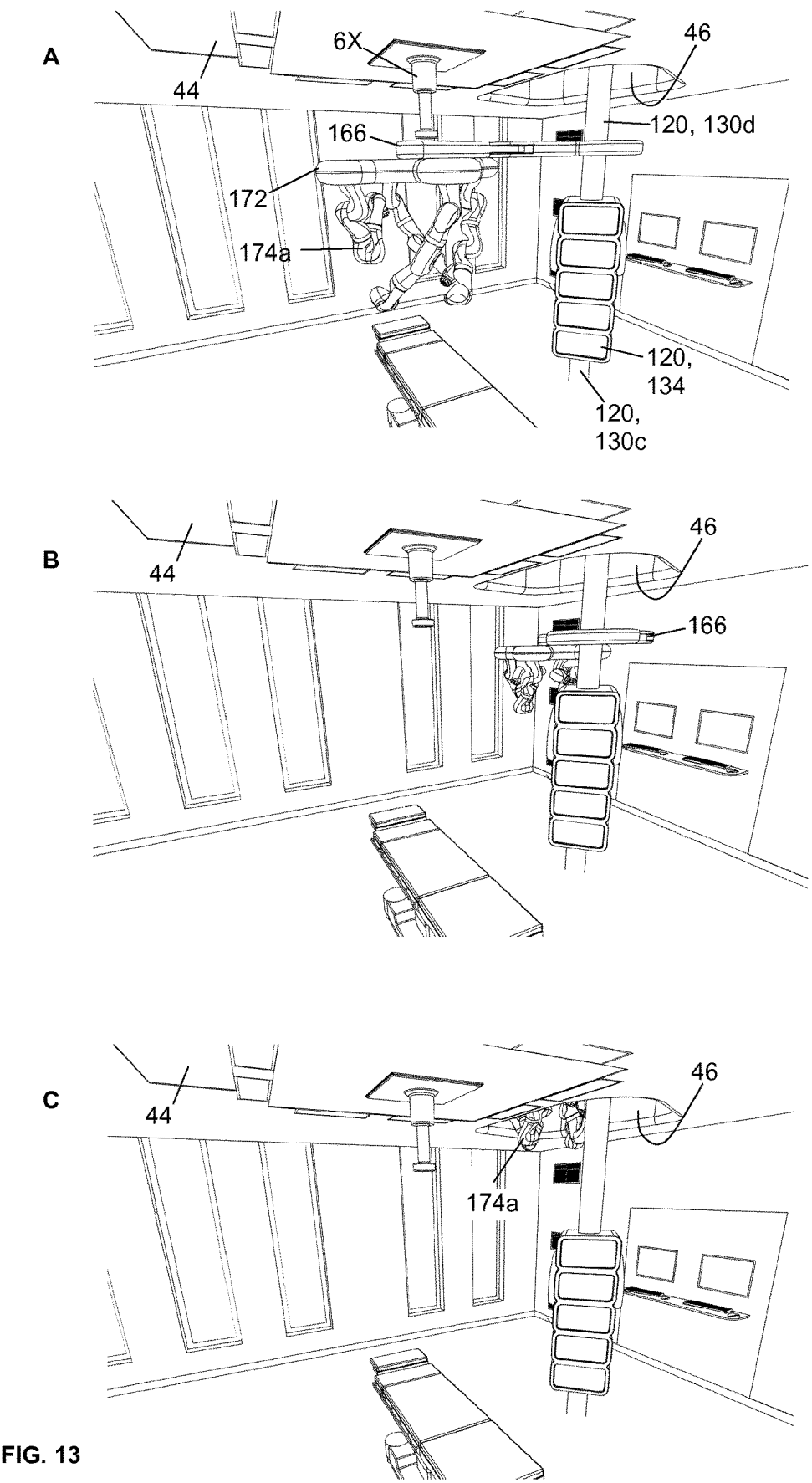

The SSU (100) may be configured such that the boom unit (160) may be folded and raised for storage in a space above a false ceiling in the room as shown, for instance, in FIGS. 13A to C.

FIGS. 11A to 12C depict different views and configurations of a structural support unit, SSU (100) for vertical fitting in an operating theatre. The SSU (100) comprises a telecopic vertical supporting part (VSP) (120) comprising a telescopic load-bearing cylindrical tube (130). The telescopic load-bearing cylindrical tube (130) comprises a base load-bearing cylindrical tube (130a) and an extendible load-bearing cylindrical tube (130b) in slidable relation to the base load-bearing cylindrical tube (130a). The upper end (40) of the VSP (120) terminates in a hub (122). The VSP (120) is supported at its lower end on a floor (22) mounted steerable dolly (126). A ceiling (42) mounted coupling (60) is provided for engagement with the upper end (40) of the VSP (120). Slidably attached to the VSP (120) is an articulated boom unit (160) having a number of arms disposed with a load that is an assembly of 3 robotic arms (144a-c) attached to a support (172). Further attached to the VSP (120) are two storage units (134, 134') and a monitor (136).

In FIGS. 11A to 11C, the SSU is in a stored mode; the boom unit (160) is folded to bringing the assembly of 3 robotic arms closer to the VSP (120) to occupy less space and move the center of gravity closer to the VSP for increased stability. In FIG. 11A VSP (120) is advanced (127) towards the ceiling (42) mounted coupling (60) by movement of the dolly (126). In FIG. 11B, the extendible load-bearing cylindrical tube (130b) is raised (129) relative to the base load-bearing cylindrical tube (130a) of the VSP (120). In FIG. 11C, the upper end of the VSP (120), more in particular the extendible load-bearing cylindrical tube (130b) is engaged in a ceiling (42) mounted coupling (60).

Figure 12A:
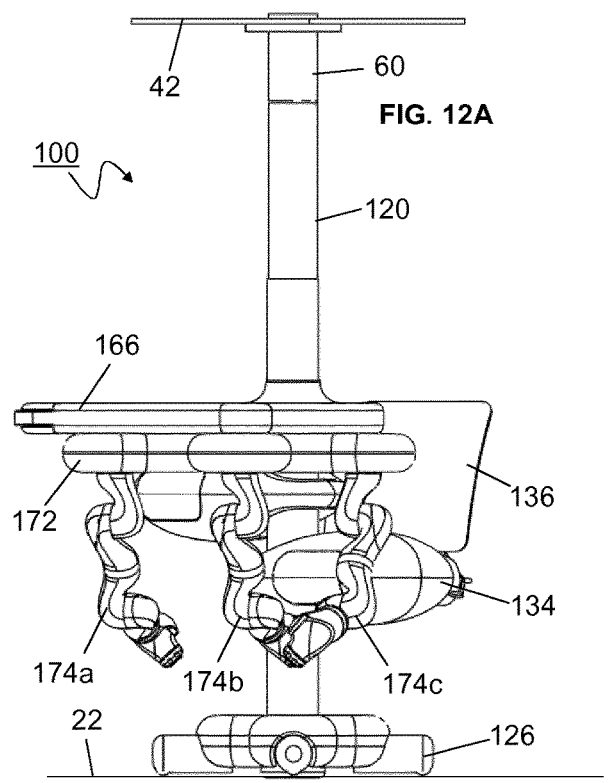
Figure 12B:
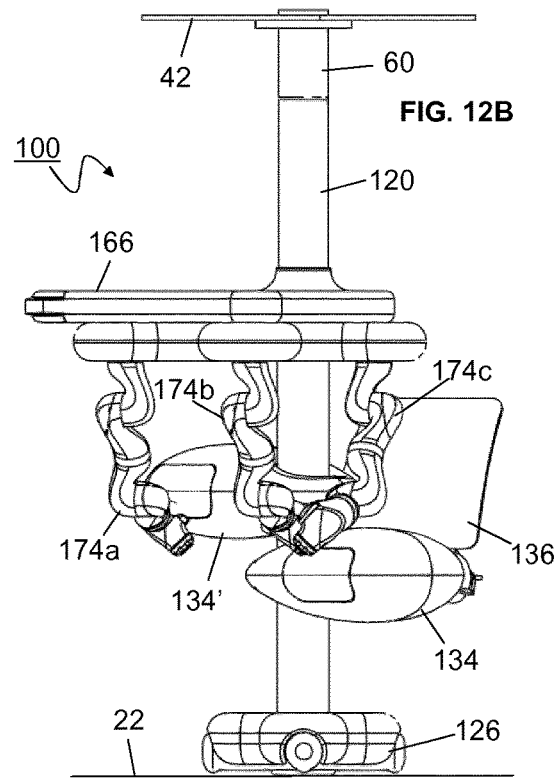
Figure 12C:
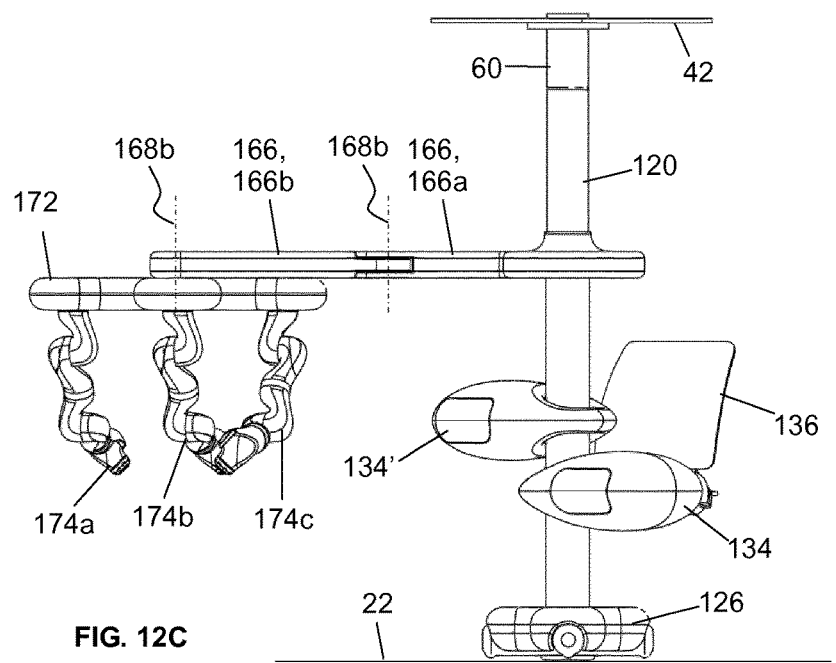

In FIGS. 12A to 12C the SSU (100) is engaged in the ceiling (42) mounted coupling (60). In FIGS. 12A and 12B the SSU (100) is in a stored mode; the boom unit (160) is folded to bringing the assembly of 3 robotic arms closer to the VSP (120) to occupy less space. In FIG. 12C, the structural support unit, SSU (100) is in an operational mode; the boom unit (160) is unfolded and the arms (166a, 166b) extended by rotation of the arms (166a, 166b) about revolute joints.

In FIGS. 13A to C a sequence of movements is shown wherein the boom unit (160) is folded and stored in a space (46) above a false ceiling (44). In FIG. 13A, the boom unit (160) is extended, in FIG. 13B, the boom unit (160) is folded and brought closer but rotation to the VSP (120). In FIG. 13C, boom unit (160) is raised by sliding along the VSP (120) into the space (46) above the false ceiling (44). The robotic arms (174a) may be visible.

The present invention provides according to a second aspect, a system (200) comprising a robotic arm, RA, configured to control a position and/or direction of a tool for working on an object and further configured to effect a change of tool from a tool storage unit (see e.g. FIGS. 15 to 19C).

The system (200) may comprise the robotic arm, RA and the tool storage unit. The system (200) may be provided in combination with the structural support unit, SSU (100) previously described. The system (200) may be mounted in relation to the assembly of one or more robotic arms (174 a-c), in particular to the support (172).

The system (200) comprises a robotic arm (220), RA, having a base end (222) and an effector end (224) and a plurality of intervening linkages connected by joints, wherein the arrangement of links and joints provides at least 6 degrees of freedom of movement to the effector end. The joints are actuatable, typically by motors, hydraulics, or pneumatics allowing control of the position and direction of the effector end by electronic signals. Each joint, also known as a kinematic pair, may offer 1 or 2 degrees of freedom (DOF) of movement, preferably 1 DOF. A joint may be a revolute or prismatic joint. A revolute joint has one degree of freedom of movement that is rotational. A prismatic joint has one degree of freedom of movement that is a linear displacement i.e. slidable. Typically a robotic arm comprises 6 joints each having 1 DOF to generate 6 DOF of movement to the effector end. Where a robot arm contains more than 6 joints, the position and direction of the effector can be attained using a plurality of different combinations of joint positions, offering redundancy that is useful for instance where the path of the robotic arm is restricted.

Figure 15:
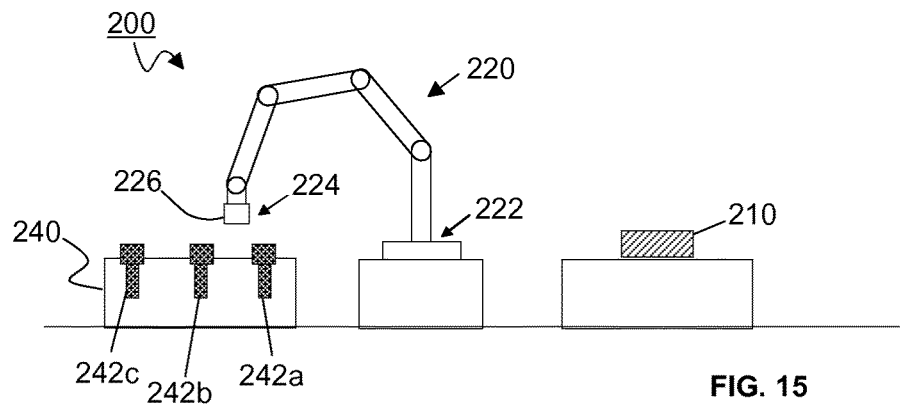

The effector end (224) is disposed with a RA fitting (226) for repeatable dismountable attachment to a tool (e.g. one of 242a-c) for working on an object (210) (see for instance, in FIG. 15). The RA fitting (226) may repeatable dismountably attach to a tool (242a-c) using a motorised connector, a spring-loaded connector, a manually-activated connector (e.g. screw, latch, bolt, bar).

The robotic arm (220) is configured to control a position and/or direction of the tool (e.g. one of 242a-c) for working on the object (210). The robotic arm (220) may be configured to control other functions such as a gripper, scissor, camera, light source etc. disposed at a distal end of the tool.

The robotic arm (200) is further configured to direct the RA fitting (226) at the effector end (204) to a tool storage unit (240) configured for holding a plurality of tools (242a-c) for working on the object.

Figure 18:
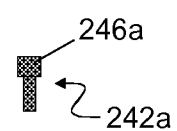

The robotic arm (200) may be configured to direct the RA fitting (226) to the tool connector (see FIG. 18 246a; FIG. 22 246a-c, FIG. 23 246i, FIG. 24 246ii, FIG. 25 410) of the tool (242), and to dismountably attach to the connector of the tool.

Figure 15A:
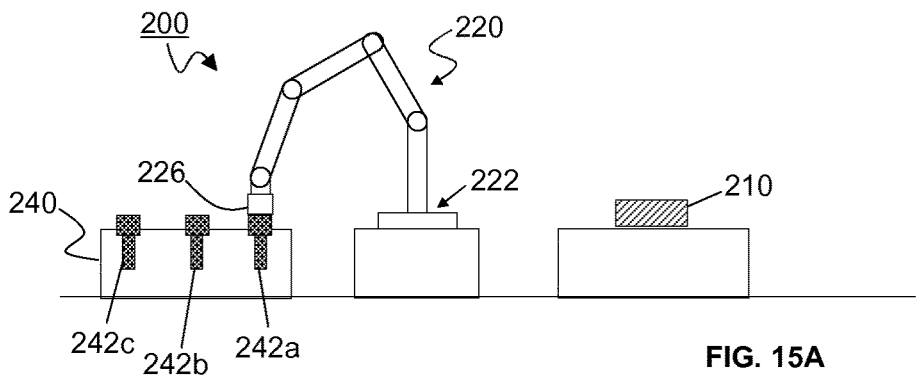
Figure 15B:
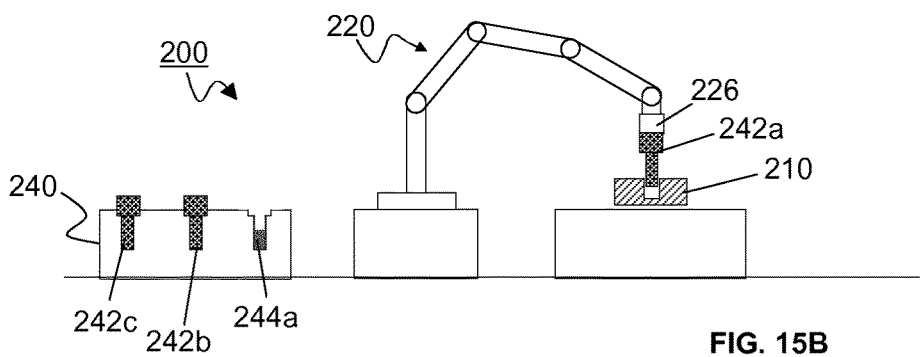

The robotic arm (200) further configured to effect attachment of a selected tool (242a) from the plurality of tools in the tool storage unit to the RA fitting (226) (see for instance, in FIG. 15A). The same robotic arm (200) is employed for working on the object (210) (see for instance, in FIG. 15B).

Figure 15C:
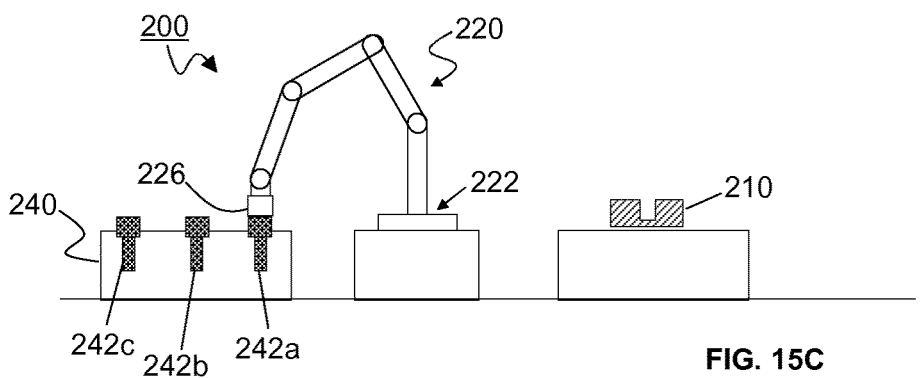

The robotic arm (200) further configured to effect return to the tool storage unit (240) of the selected tool (242a) to its location (see for instance, in FIG. 15C), and detachment from the RA fitting (226).

A controller may be connected to the robotic arm to provide control signals to effect tools selection and control of the tool The robotic arm may be configured for any application e.g. surgical, industrial, engineering, and manufacturing. It is preferably a surgical robotic arm, and the tool is preferably a surgical instrument. A robotic arm that can perform both a surgical procedure (e.g. incisions and minimally invasive surgery)

Figure 16:
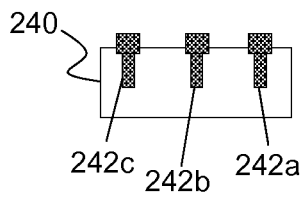
Figure 17:
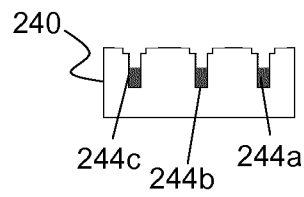

The tool storage unit (240) configured for holding a plurality of tools (242a-c) for working on the object (see for instance FIG. 16). Each tool (242a-c) of the plurality of tools may be held in a different location in the tool storage unit (240).

The tool storage unit (240) may comprise a plurality of fixed-position locators (244a-c) one for each of the plurality of tools (see for instance FIGS. 15A to 15C, and 17). Each locater (244a-c) may contain a recess to receive the tool or coupling for attachment to the tool or to a packaging containing the tool.

The tool storage unit (240) comprises a moveable selector (e.g. carousel) configured to offer a selected tool from the plurality of tools for attachment to the RA fitting.

The tool (242a-c) may be any for surgical, engineering and industrial applications. Preferably it is for surgical application. Examples of surgical tools include: standard surgical instrument—knife, scissors, suction tube, trocar, Verass needle ultra sound probe, c-arm, controller fora magnetic intracorporeal camera, catheter, HF coagulator tool, wherein the RA fitting is provided with a coupling for supply of signals and power to the HF coagulator tool. A Veress needle is used to initiate insufflation. It is introduced into the abdomen to insufflate it with gas (e.g. $CO_2$). Once the abdomen is sufficiently insufflated it becomes safe to introduce the trocars.

The tool may be a surgical instrument, such as, for instance, a minimally invasive surgical instrument, a laparoscopic instrument, and endoscopic instrument, or an endovascular catheter.

The tool may be a steerable articulated instrument such as but not limiting to endovascular, endoscopic, neurosurgical, ENT (ear, nose and throat), orthopaedic applications, surgical instruments, robotic tele-operated medical robotics or hand-held surgical tools, and industrial and engineering applications. The steerable articulated instrument may have an end effector may comprise any suitable tool for a remotely controlled application, such as a screw driver, abrasive pad, drill bit, gripper, pliers, cutting scissors, camera and the like. The steerable articulated instrument end effector may be any tool useful in a surgical procedure, tasks as gripper, pliers, cutting scissors, needle holder, retractor, camera needle, (aspiration) catheter, electrical catheter, optical (laser) fiber, ultrasound therapy, measurement probe (temperature, pH, pressure, electrophysiology), stapler, drill, electro-coagulator, HF, clip applier, fluid port and the like.

The steerable articulated instrument may be that described in, for instance, WO 2009/098244, WO 2016/030457, WO 2016/091857, WO 2016/091858.

Figure 25:
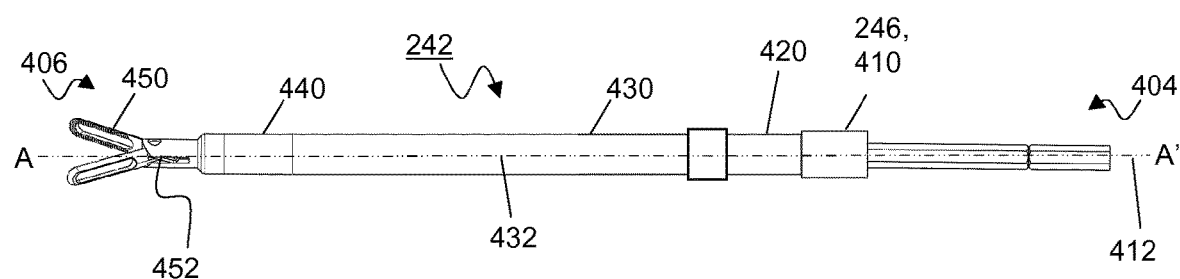

The tool (442) may be a tool steerable and controllable by a robotic arm, having a proximal end (404) and a distal (406) end comprising:
- a shaft (430), a bendable proximal part (420) and a bendable distal part (440),
- a connector (410) configured for dismountable attachment to the robotic arm, attached in fixed rotational relation to the bendable proximal part (420),
- an end effector (450) attached in fixed rotational relation to the bendable distal part (440),
- the tool (402) configured such that:
  - the bendable distal part (440) bends responsive to bending of the bendable proximal part (420), and the end effector (450) is rotatable when the bendable distal part (440) is in a bent position by a complementary rotation of the connector (410), thereby providing control of the shaft (430) direction, bending of the bendable distal part (440), and rotation of the end effector (450) through robotic movement of the connector (410). An example of a steerable tool is shown in FIG. 25. The tool (442) may be further comprised in the system (200).

A tool connector (see FIG. 18 246a; FIG. 22 246a-c, FIG. 23 246i, FIG. 24 246ii, FIG. 25 410) is provided at a proximal end of the tool, configured for repeatable dismountable attachment to the fitting (226).

Figure 22:
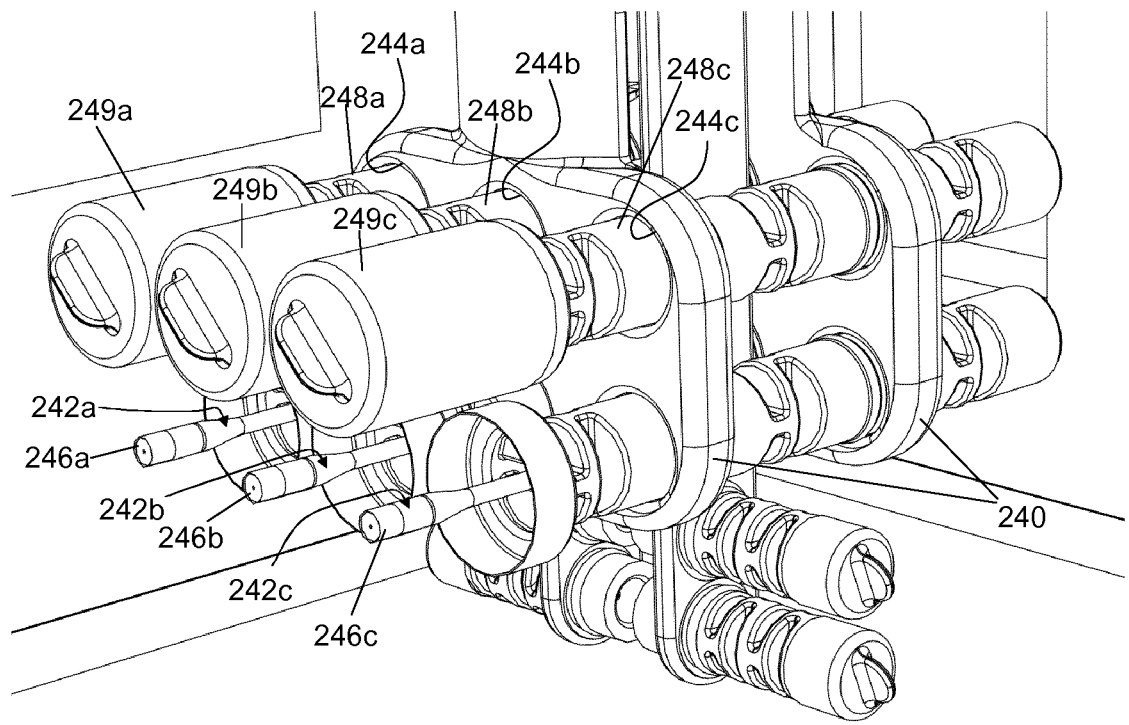
Figure 23:
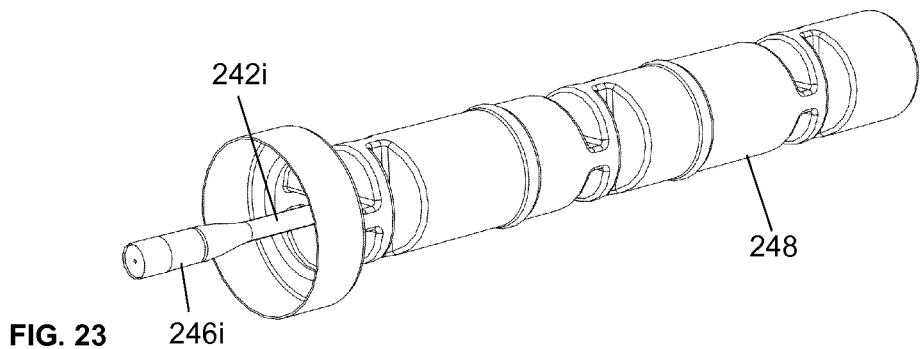
Figure 24:
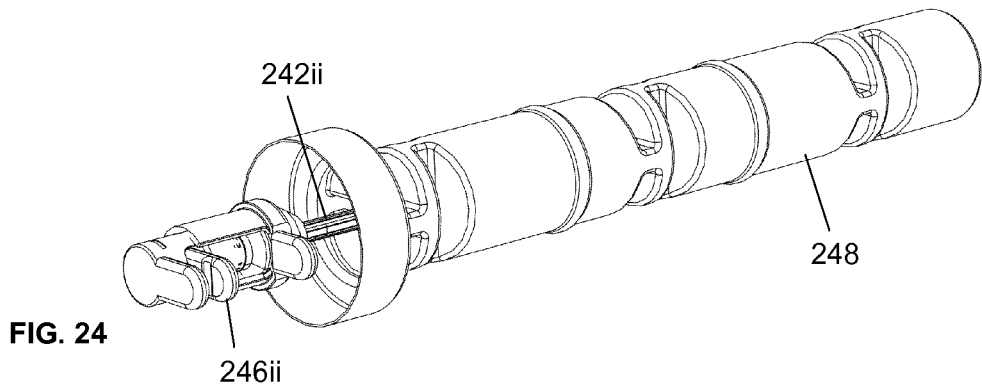

The tool storage unit (240) may be configured to receive a tool provided in a sterile packaging (248, 248a-c, see for instance, FIGS. 22-24). Each locater may contain a coupling for repeatable dismountable attachment to a packaging containing the tool.

A tool package for use with the system described herein, comprises a sterile packaging, and a tool disposed in the sterile packaging. The sterile packaging is configured for dismountable attachment to the tool-storage unit, in particular to the coupling of the locater. The sterile packaging may be configured for repeatable dismountable attachment to the tool to the sterile packaging.

Advantageously, by using a tool package, there is no need to sterilise the parts of the tool storage unit. Further, there is no need for a "sterile" nurse to load the tool storage unit (240).

Figure 19A:
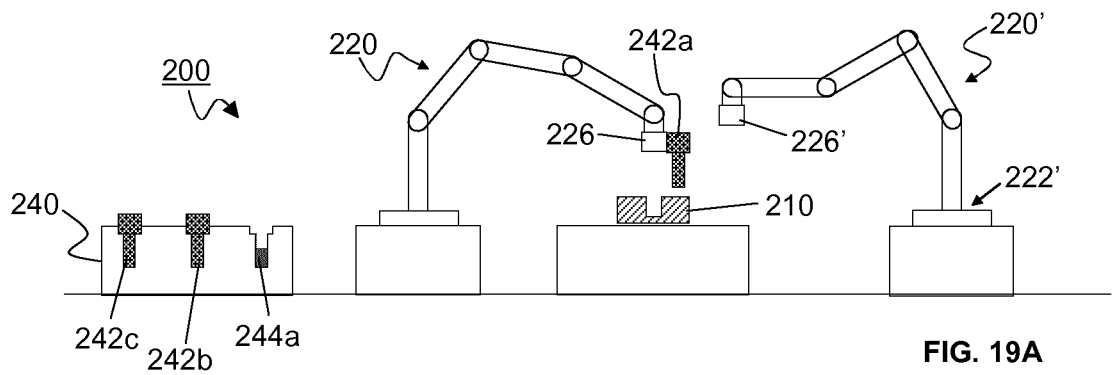
Figure 19B:
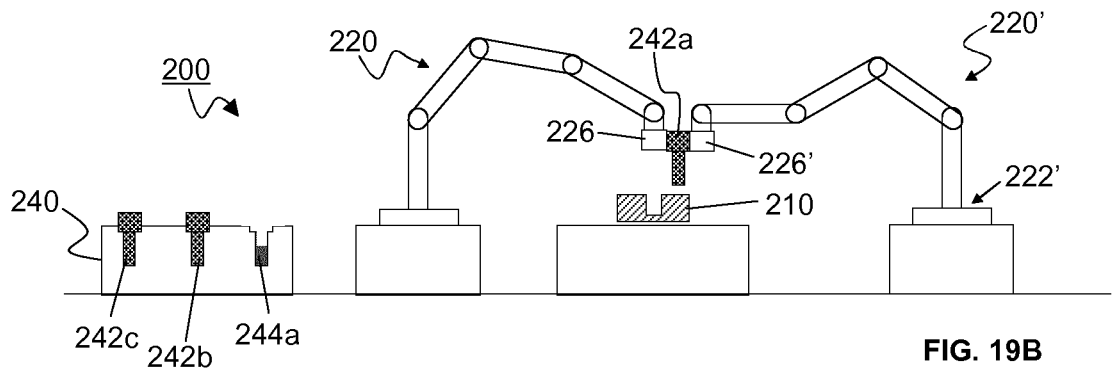
Figure 19C:
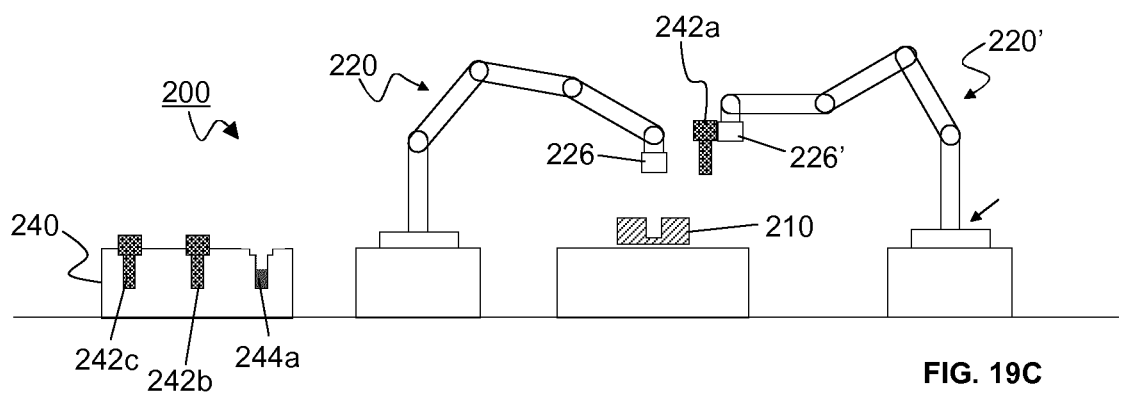

The system according may comprise one or more further robotic arms (220'), wherein the tool (242a-c) and RA fitting (226) are configured for a transfer of the tool from the robot arm (220) to one of the further robotic arms (220') (see FIGS. 19A-C). In FIG. 19B, the tool 242a is transferred from the robot arm (220) to the further robotic arms (220') Direct transfer between robotic arms may be facilitated by the tool connector (246a, 410) at the tool proximal end, which support simultaneous attachment of two RA fittings (226, 266')

The system (200) may be disposed with a (contactless) position sensing device (e.g. camera) and controller configured to determine from the position sensing device a position of a distal end of the tool for automated docking of the distal end of the tool into a working space. When the system (200) is for example used in laparoscopic surgery, it is convenient that the robotic arm can automatically dock the surgical tool into a trocar inserted into the patient.

Figure 20:
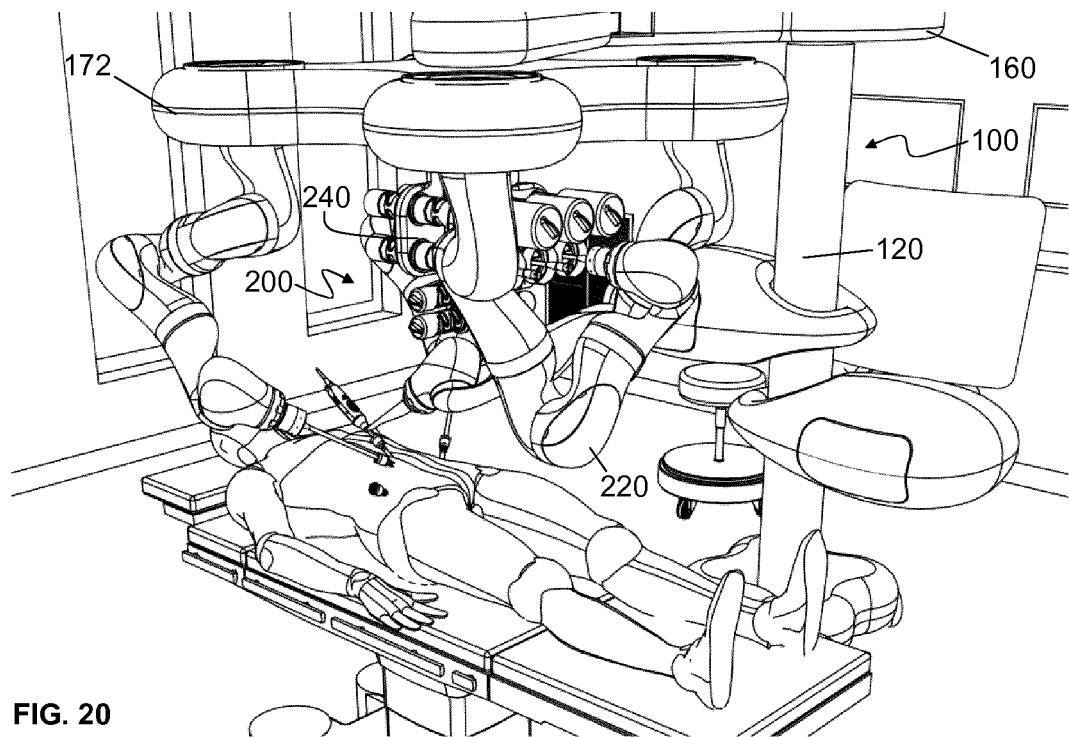
Figure 21:
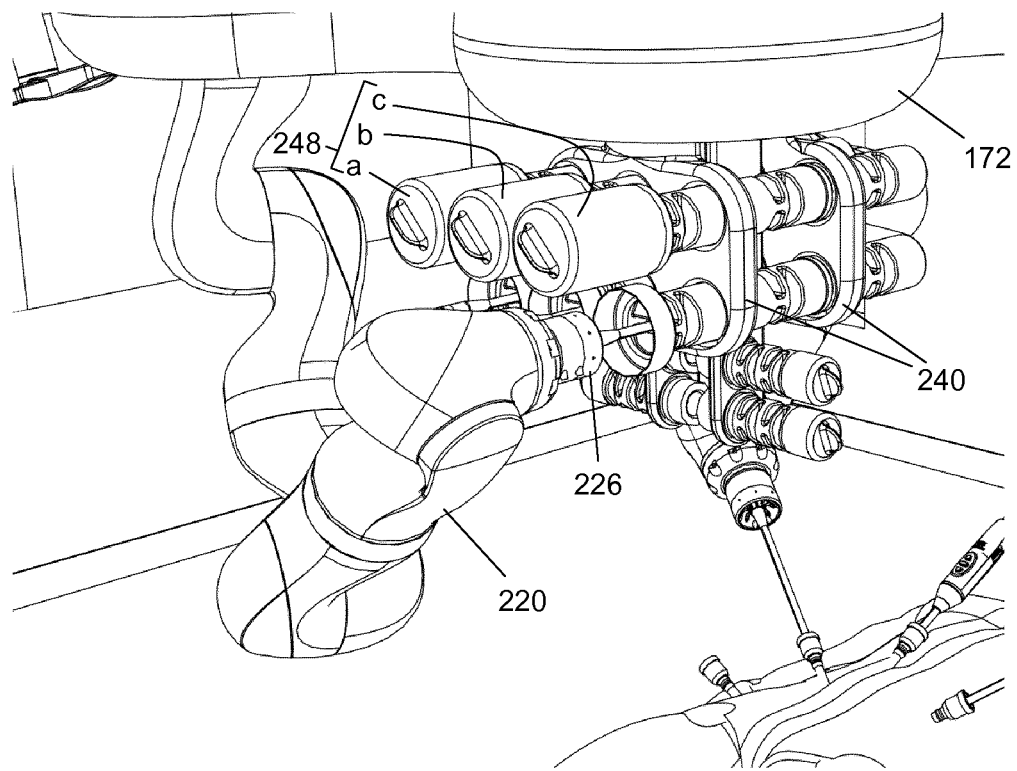

FIG. 20 depicts an exemplary system (200) installed in an operating theatre. The robotic arm (220) is attached to a SSU (100) described elsewhere herein. The SSU (100) comprises a floor- and ceiling-supported VSP (120) in connection with a slidable boom unit (160). A load of the boom unit (160) is an assembly of 3 robotic arms (e.g. 220) each attached to a revolute support (172). A tool storage unit (240) is provided in attachment to the revolute support (172) as shown in FIG. 21 which is a detail of FIG. 20. FIG. 21 shows the tool storage unit (240) disposed with a plurality of tool sterile packages (248a-c), and also the RA fitting (226) of the robotic arm (220). FIG. 22 is a view of the tool storage unit (240) disposed with a plurality of fixed-position locators (244a-c) one for each of the plurality of tool sterile packages (248a-c). Each tool sterile package (248a-c) holds a tool (e.g. 242a-c) and may be opened by removing a cap (249a-c). Each tool (242a-c) is provided at a proximal end with a tool connector (246a-b) for coupling with a RA fitting (226). FIG. 23 shows a sterile packaging (248) disposed with one type of tool (242i) having an axial push fit tool connector (246i); an end effector and optionally a motion restrictor may be deployed using a TRAA described elsewhere herein. FIG. 24 shows a sterile packaging (248) disposed with another type of tool (242ii) having a tool connector (246ii) with 2 sliders for actuation of an end effector and a motion restrictor. FIG. 25 shows a tool (242) that is a steerable instrument.

The present invention provides according to a third aspect, a tool assembly (400) comprising a tool (402) that is steerable and controllable by a robotic arm (200), the tool (402) having a proximal end (20) and a distal (40) end, the tool assembly (400) further comprising a deployable motion restrictor (460), configured to restrict bending of a straightened bendable proximal part (420) of the tool after deployment. It may optionally in addition straighten a bent bendable proximal part (420).

When a surgical tool that is an articulated steerable tool is removed from the trocar, the instrument may already be straightened, in which case the deployable motion restrictor (460) prevents bending.

As shown in FIGS. 20 to 23 for example, the tool assembly (400) comprising
- a tool (402) that is steerable and controllable by a robotic arm (200), having a proximal end (20) and a distal (40) end. The tool (402) comprises:
- a shaft (430), a bendable proximal part (420) and a bendable distal part (440),
- a connector (410) configured for dismountable attachment to the robotic arm, attached in fixed rotational relation to the bendable proximal part (420),
- an end effector (450) attached in fixed rotational relation to the bendable distal part (140),
- the tool (400) configured such that:
  - the bendable distal part (440) bends responsive to bending of the bendable proximal part (420), and the end effector (450) is rotatable when the bendable distal part (440) is in a bent position by a complementary rotation of the connector (410), thereby providing control of the shaft (430) direction, bending of the bendable distal part (440), and rotation of the end effector (450) through robotic movement of the connector (410).

The tool assembly (400) may further comprise a deployable motion restrictor (460), configured to restrict bending of and optionally straighten the bendable proximal part (420) after deployment.

The shaft (430) may pivotable around a fulcrum zone on the shaft and changes direction responsive to a complementary movement of the connector. The direction of the shaft refers to its angular placement. Changing a direction of the shaft is achieved typically by a pivoted rotation around a fulcrum zone. The fulcrum zone coincides with a longitudinal axis (A-A') of the shaft, for instance, a central longitudinal axis of the shaft. Such movements have two degrees of freedom (2-DOF), and may be known as pitch and yaw. When referring to direction, two degrees of freedom is equivalent to a rotation about two axes. The fulcrum zone is where axes of rotation intersect. The fulcrum zone typically coincides with an entry point to the space being investigated, for instance with a hole made in a wall, membrane or port. The fulcrum is provided by the entry point. Where the steerable instrument is a laparoscopic medical instrument, the fulcrum zone is placed at a bodily incision where the laparoscopic medical instrument is introduced. The minimally invasive instrument is typically enters the body via a trocar—a tube-like port inserted into an incision—that supports the steerable instrument and is amendable to pivoted rotation around the fulcrum point of the incision.

The motion restrictor (460) may comprises a rigid member disposed in slidable relation to the connector (410) configured to span the bendable proximal part (420) and at least part of the connector (410) when deployed. It may clear the bendable proximal part (420) when retracted.

Figure 29:
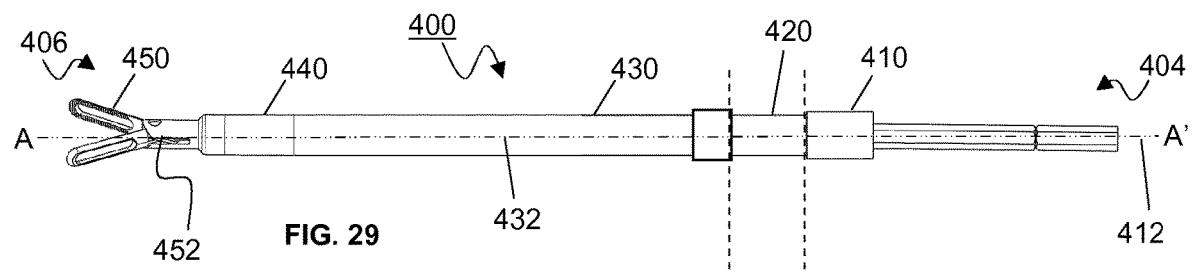
Figure 29A:
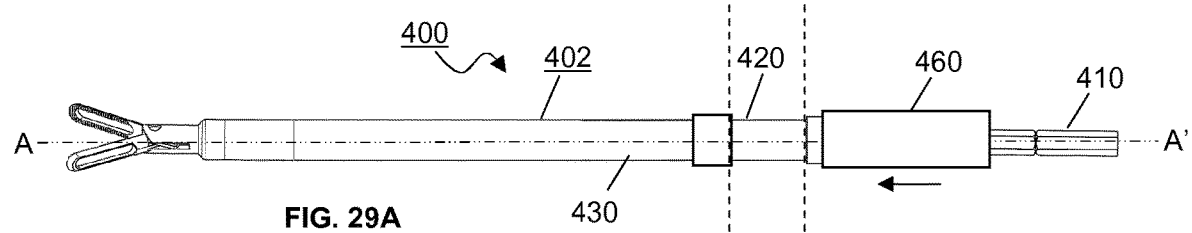
Figure 29B:
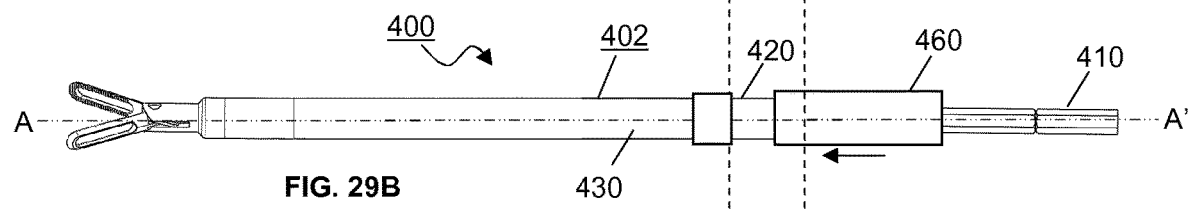
Figure 29C:
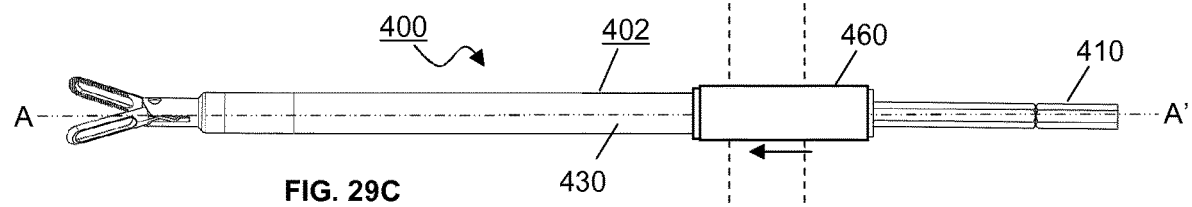

In FIG. 29, a steerable tool is shown without the motion restrictor (460). In FIG. 29A, the motion restrictor (460) is in a non-deployed (not straightening) position. In FIG. 29B, the motion restrictor (460) is partially non-deployed. In FIG. 29C, the motion restrictor (460) is fully non-deployed, preventing bending of the proximal bending part (420), and consequently of the proximal distal part (412).

Figure 45:
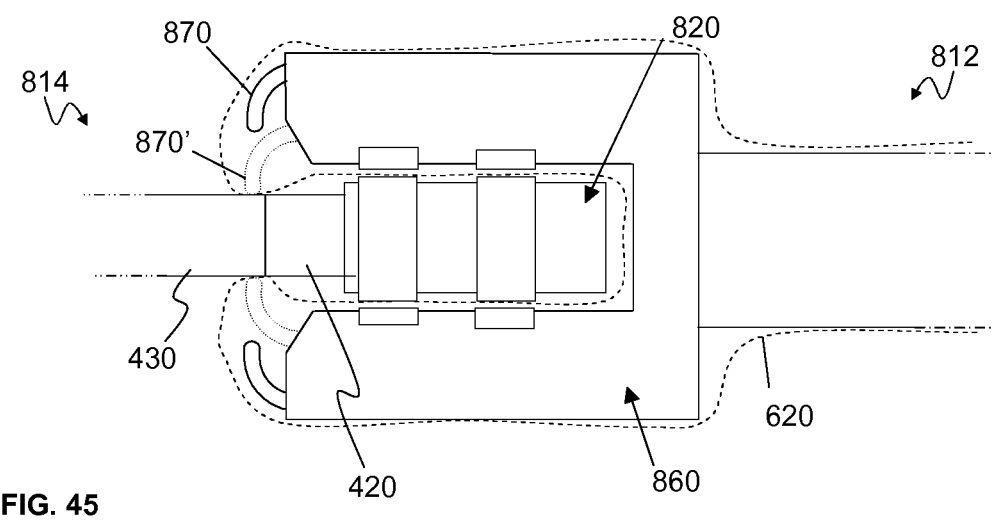

A motion restrictor may be provided in a robotic arm fitting (860) and comprise a rigid member (e.g. curved rod, see FIG. 45, 870, 870') disposed in radial-slidable relation to the attached connector (410) configured to apply a radial force to the shaft region (430) when deployed. Force of the motion restrictor (870, 870') deployed against the shaft region (430) prevents the proximal bendable part from bending.

The rigid member may comprise a rigid sleeve, slidable in a distal direction for deployment, and retractable in a proximal direction to release the bendable proximal part (420) for bending. The deployable motion restrictor (460) is hence advanced in a distal direction to straighten and lock the bendable distal part (440) and in the proximal direction to unlock the bendable distal part (440). Automated control of the locking is simplified because it avoids sliding the deployable motion restrictor (460) over the shaft that requires a linear actuator to be added to the shaft which can destabilize the tool, whereas the present sleeve slides proximal of the proximal bendable part and can be integrated into the last link of the robotic arm. Hence, there is improved instrument stability. Further there is no compression of the shaft as the linear actuator does not need to be clamped to the shaft, thereby allowing the diameter of the shaft to be reduced.

The tool may be a tool as described elsewhere herein. The tool may be that described in, for instance, WO 2009/098244, WO 2016/030457, WO 2016/091857, WO 2016/091858.

The fitting disposed on the robot effect end may comprise a slidable coupling configured to couple with the motion restrictor (460), and for deployment and retraction of the motion restrictor.

Figure 30:
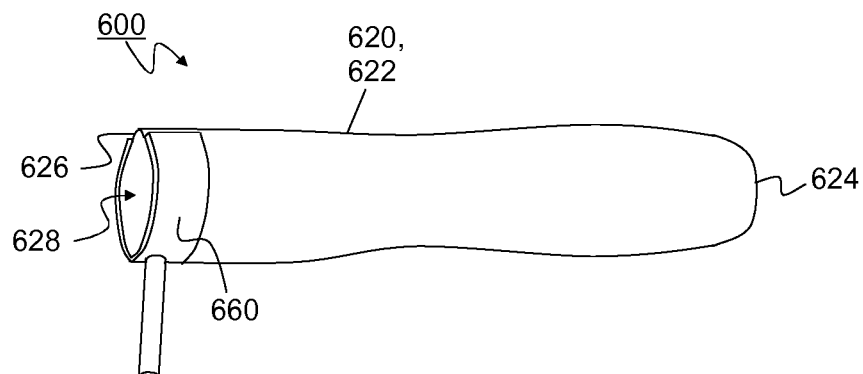
Figure 31:
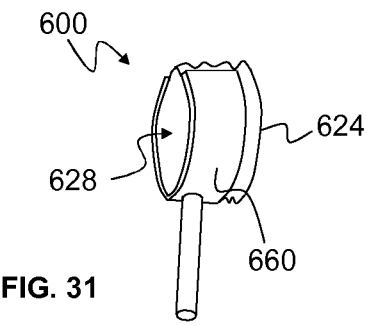
Figure 32:
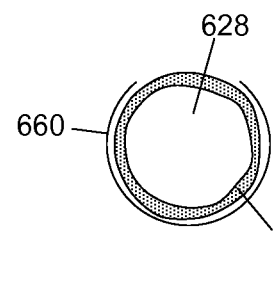
Figure 33:
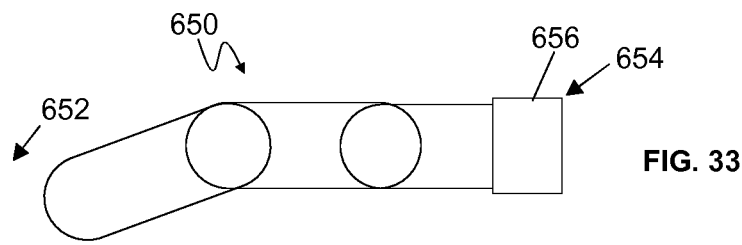

The present invention provides according to a fourth aspect, a dispenser unit (600) as shown, for instance in FIGS. 30 to 32, for applying a sterile drape (620) over a surgical robotic arm (650) having a base end (652) and an effector end (654). An effector end (654) of a robotic arm (650) is depicted in FIG. 33. The robotic arm (650) at the effector end is disposed with a fitting (656) for repeatable dismountable connection to a tool or tool assembly. The tool or tool assembly may be one as described elsewhere herein. The fitting (656) may be configured for control of the deployable motion restrictor (460) as described herein.

Figure 34A:
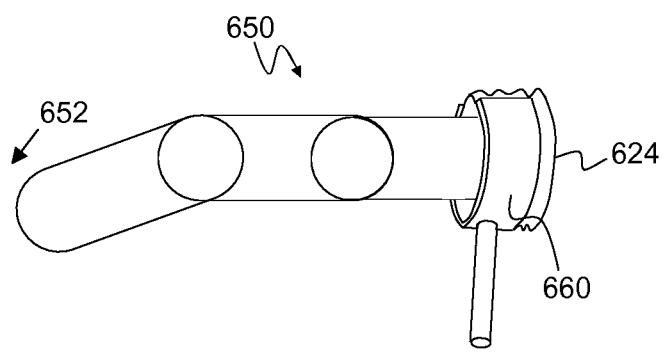
Figure 34B:
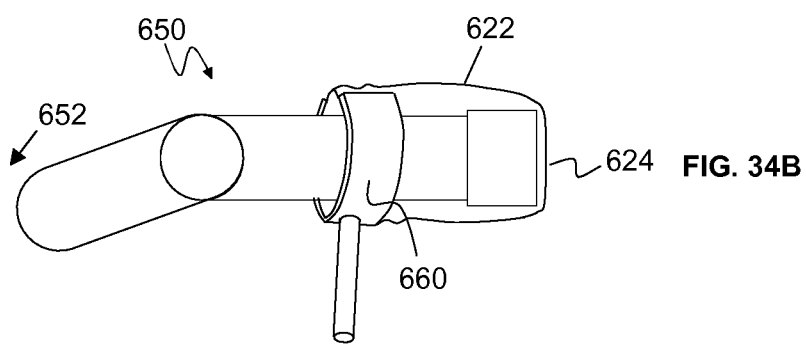

The dispenser unit (600) comprises a sterile drape (620) with longitudinal sleeve (622) form closed at one end (624) and open at the other end (226), folded so as to reduce its longitudinal length while maintaining a passage (628) through the folded sleeve to the closed end. In FIG. 30, the longitudinal sleeve (622) is in a longitudinal unfolded state. In FIG. 31, the longitudinal sleeve (622) is in a longitudinal folded state. FIG. 33 shows an end view of the dispenser unit. The open end (626) of the longitudinal sleeve (622) is fixed to the open end (626) of the longitudinal sleeve. The open end (626) of the longitudinal sleeve (622) may be detachable or non-detachably fixed to the open end (626) of the longitudinal sleeve. The passage (628) of the longitudinal sleeve (622) is configured to receive the robot arm (650), in particular leading from the effector end (654). The closed end (624) of the longitudinal sleeve (622) is configured to abut with robot arm effector end (654). In FIG. 34A the closed end (624) is in coupling arrangement with the robotic arm (650) effector end (654). The dispenser unit (600) configured to unfold the longitudinal sleeve over the robotic arm by movement of the applicator (660) or robotic arm (650) to bring the applicator (660) closer to the base end (652) of the robotic arm (650). In FIG. 34B the applicator (660) is closer to the base end (652) of the robotic arm (650), and the longitudinal sleeve (622) is partially unfolded over the robotic arm (650). At the end of the movement, the longitudinal sleeve (622) is fully unfolded over the robotic arm (650). The longitudinal sleeve (622) may be detached from the applicator (660). The applicator (660) may remain attached to the longitudinal sleeve (622), and dismountably fixed to the robot e.g. by magnets; the handle where present may be detachable.

The applicator (600) comprises an open frame for fixing, optionally detachably, to the open end (626) of the longitudinal sleeve (622). It may have an annular shape, a segment of an annulus shape. It may be provided with a handle. It may be provided in fixed relation to a coupling (632) for automated robotic draping. It may be made from a rigid material.

The longitudinal sleeve (622) is typically made from a flexible polymeric sheet, and is usually transparent.

The open end (626) of the longitudinal sleeve (622) may be provided with one or more magnetic clasps, configured for dismountable attachment to the robotic arm (650).

The longitudinal sleeve (622) couples with the fitting (656) at the effector end (654) of the robotic arm (650), in particular at the closed end (624) of the longitudinal sleeve (622). Where the fitting (656) merely grips the tool or tool assembly, control of the tool or tool assembly can be effected by gripping it through the longitudinal sleeve (622) or sterile drape (620). The flexibility of the longitudinal sleeve permits through-sleeve gripping.

The sterile drape (620) may further comprise one or more interface elements (e.g. FIG. 37H, 638a-c). An interface element comprises a body disposed in a wall of the longitudinal sleeve (622), typically at or towards the closed end (624). The body may be injection moulded or deep pressed or vacuum melted. The body may be stiffer (e.g. more rigid) or more elastic compared with the wall of the longitudinal sleeve (622). The wall of the longitudinal sleeve (622) is typically sealed around or over the edges of the interface element to ensure a sterile barrier. The interface element body has a passage side facing the passage (628) of the sleeve, and an outer side facing the exterior of the sleeve (622). The interface element body is configured to dismountably attach on the passage side to the robotic arm (650) fitting (656), and dismountably attach on the outer side to the tool or tool assembly at the proximal end. The body is shaped on the passage side for coupling with at least a part of the robotic arm (650) fitting (656). The body is shaped on the outer side for coupling with at least a part of the tool or tool assembly, for instance, to a connector thereon. The interface element transmits forces from the robotic arm (650) fitting (656) to the tool or tool assembly. An interface element preferably has no moving parts thereby ensuring no ingress of particles (e.g. dirt, bacteria etc) into the passage (628) of the sleeve (622).

The interface element may allow the robotic arm (650) fitting (656) to substantially support and control movement of the tool or tool assembly.

Where the tool or tool assembly at the distal end is disposed with an end effector such as a gripper and at a proximal with a proximal actuator therefor, an interface element may be provided for coupling with the proximal actuator allowing robotic actuation thereof through the robotic arm (650) fitting (656).

As mentioned elsewhere herein, the tool assembly may comprise a tool disposed with a deployable motion restrictor. An interface element may be provided for coupling with the deployable motion restrictor allowing robotic actuation thereof through the robotic arm (650) fitting (656).

The interface element may be disposed with one or more electrical contacts for the transmission or electrical power, data signals to and/or from the tool. Where the tool is an HF coagulator tool, wherein the contacts transfer signals and/or power from the robotic arm (650) fitting (656) to the HF coagulator tool.

Figure 35:
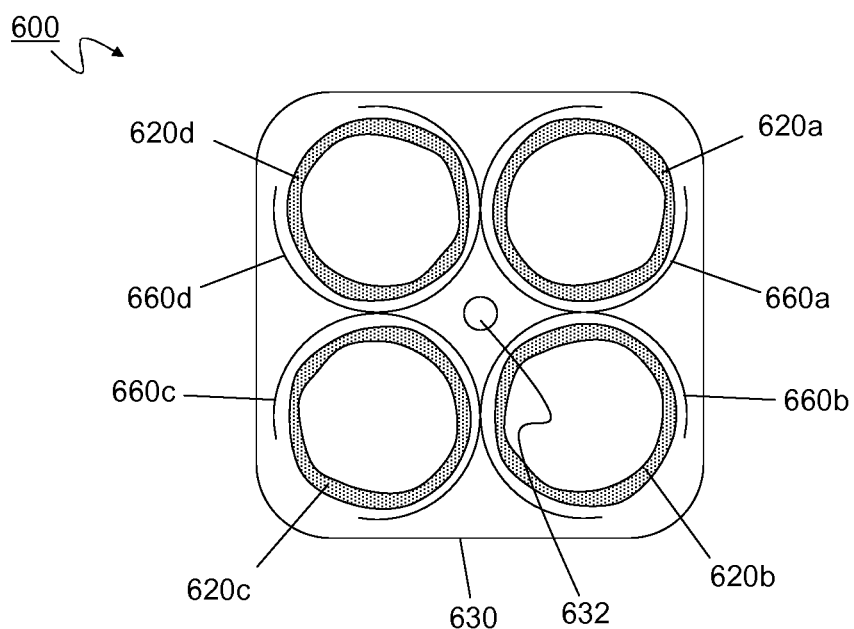
Figure 36A:
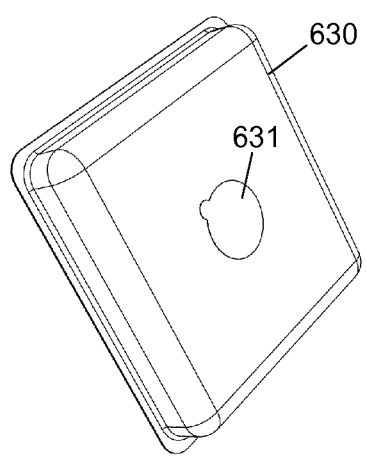
Figure 36B:
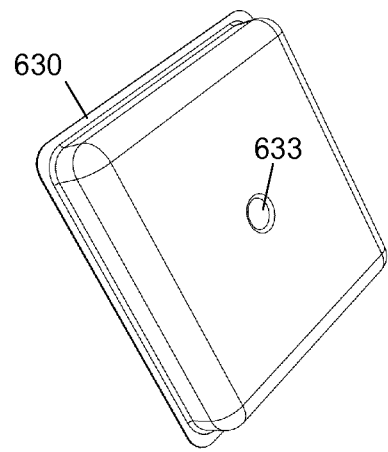

The dispenser unit (600) may comprise a plurality of applicators (660a-d) and sterile drapes (620a-d) detachably fixed thereto (see for instance FIG. 35). The applicators (660a-d) may be attached to one or more other applicators in the dispenser unit. The plurality of applicators (660a-d) may be disposed in fixed relation to a coupling (632) for assisting with automated robotic draping. The plurality of applicators (660a-d) may be housed in packaging (630). Examples of packing are shown in FIGS. 36A and 36B. A body of the packaging is provided with a removable seal (631) that covers an aperture (633) is alignment with the aforementioned coupling (632).

FIGS. 37A-H depicts a sequence of automated draping of a robotic arm. It is illustrated using the structural support unit, SSU (100) as described elsewhere herein, however, it is to be appreciated automated draping of a robotic arm could be facilitated using any fixed support.

Figure 37A:
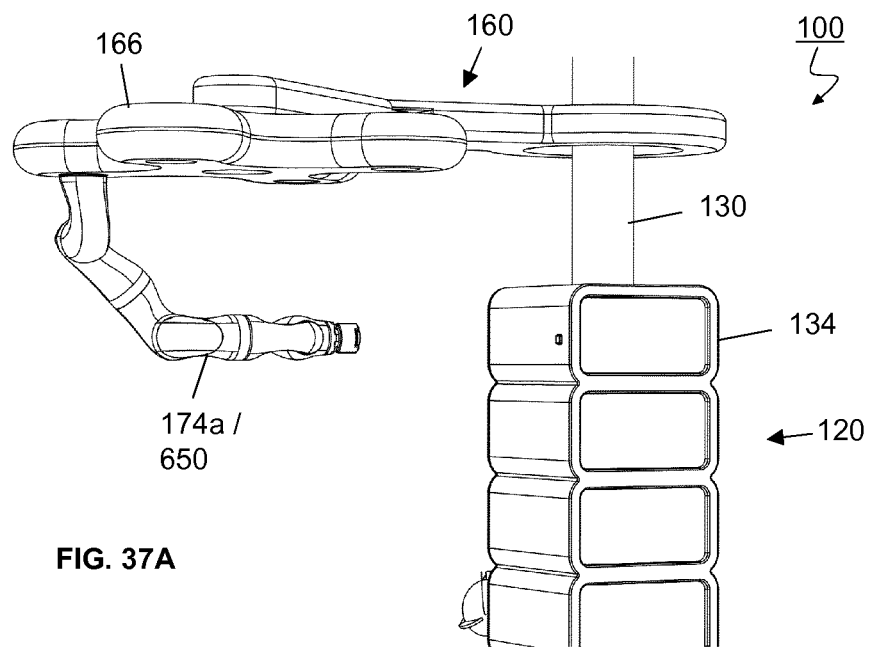

FIG. 37A depicts the structural support unit, SSU (100) as described elsewhere herein, a vertical supporting part (VSP) (120) having a load-bearing cylindrical tube (130c,d) and a load bearing (vertical) storage unit (134). The boom unit (160) is disposed essentially horizontally with respect to the VSP (120), and load of the boom unit (160) is an assembly of one or more robotic arms (174a-c); only one arm is shown (174a/650).

Figure 37B:
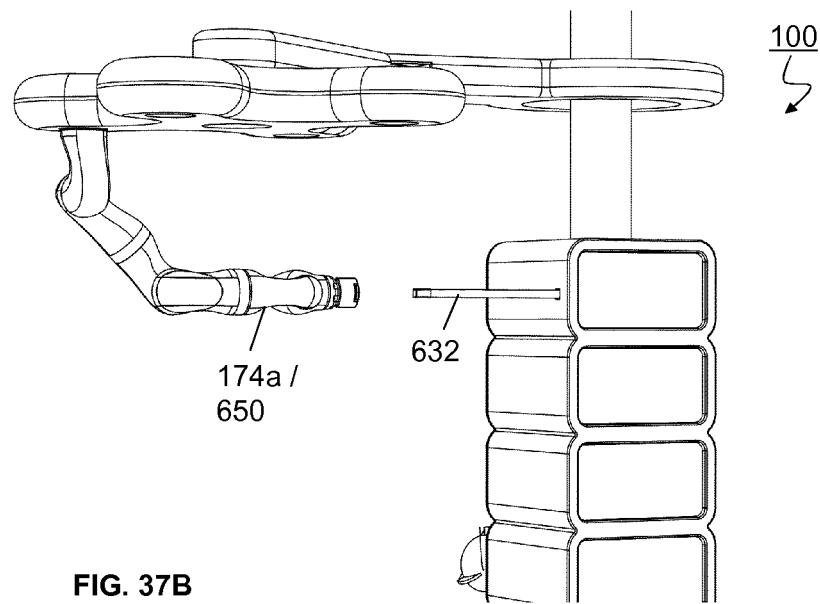

In FIG. 37B, a rigid spacing rod (634) is advanced from the storage unit (134), the end of which couples with the coupling (634) provided in fixed relation plurality of applicators (660a-d).

Figure 37C:
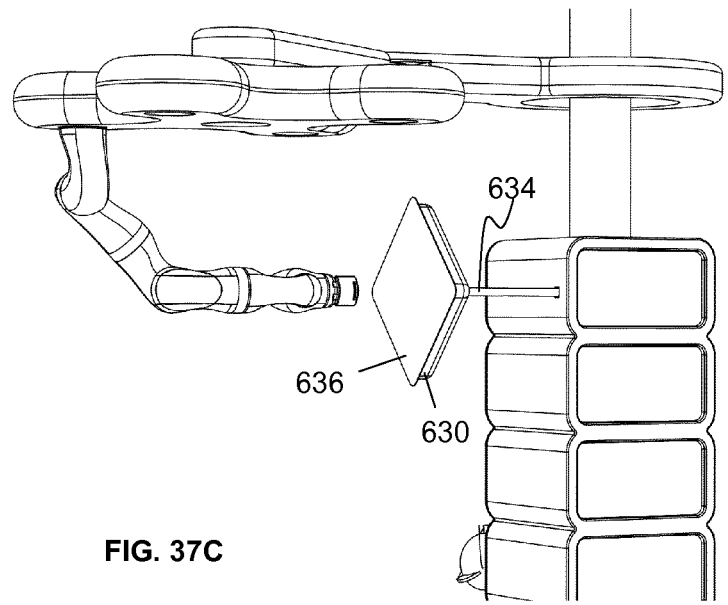

In FIG. 37C, the rigid spacing rod (634) is attached (by a nurse, for example) to the coupling (632) of the applicators (660a-d), which applicators are housed in a packaging (630) of the type shown in FIGS. 36A and 36B. An aperture (633) in the reverse side of the package (630) allows access to the coupling (632). A front side of the packaging is sealed with a cover (636).

Figure 37D:
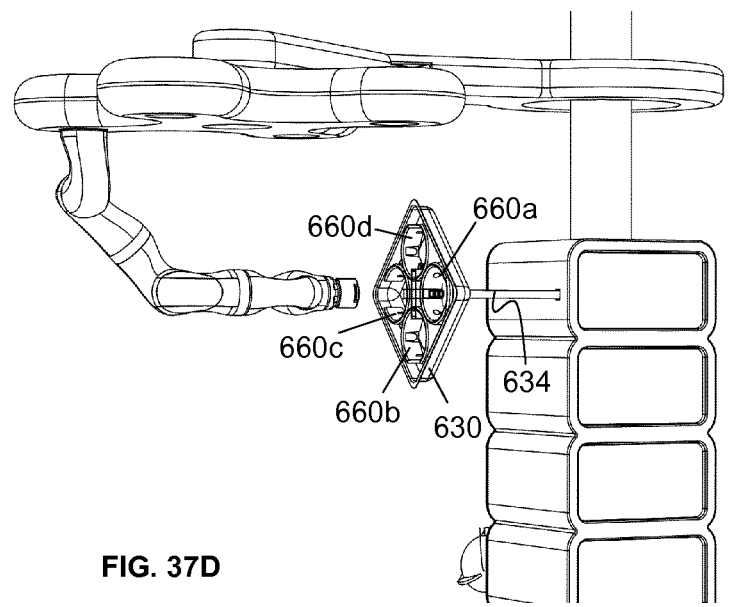

In FIG. 37D, the cover (636) has been removed from front side of the package (630), revealing plurality of applicators (660a-d), in similar arrangement to that shown in FIG. 35.

Figure 37E:
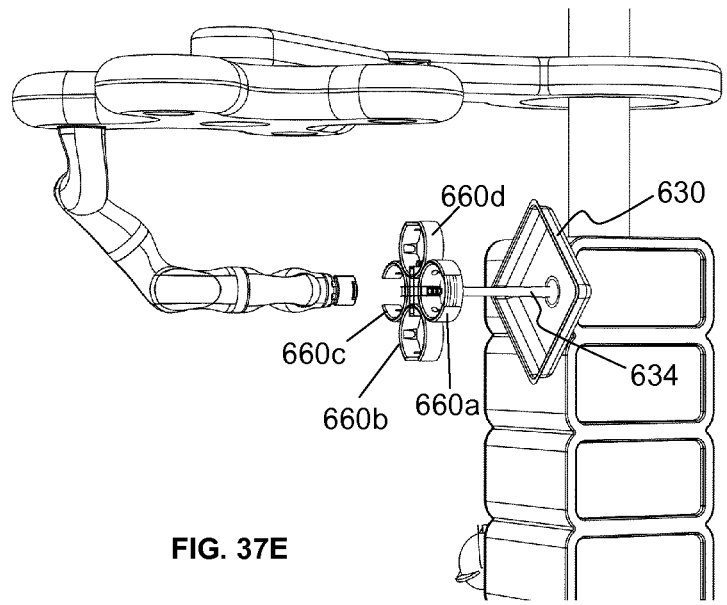

In FIG. 37E, the package (630) is pushed back (e.g. by a nurse), travelling through the aperture (633) across the spacing rod (634), to provide clearance behind the applicators (660a-d) for advancement of the robotic arm (174a/650) through the passage of the longitudinal sleeve. A compressed sterile drape is disposed between and fixed in relation to the coupling (634) at one end and the aperture (633) at the other end. Pushing the package (630) back applies tension to the compressed sterile drape, to extend it over the spacing rod (634) to cover the rod. It prevents unwanted contact of the sterile drape (620) with the unsterile spacing rod (634).

Figure 37F:
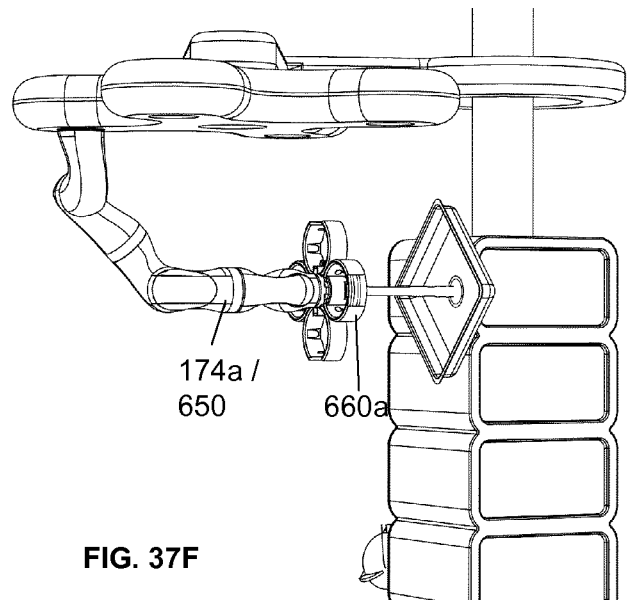
Figure 37G:
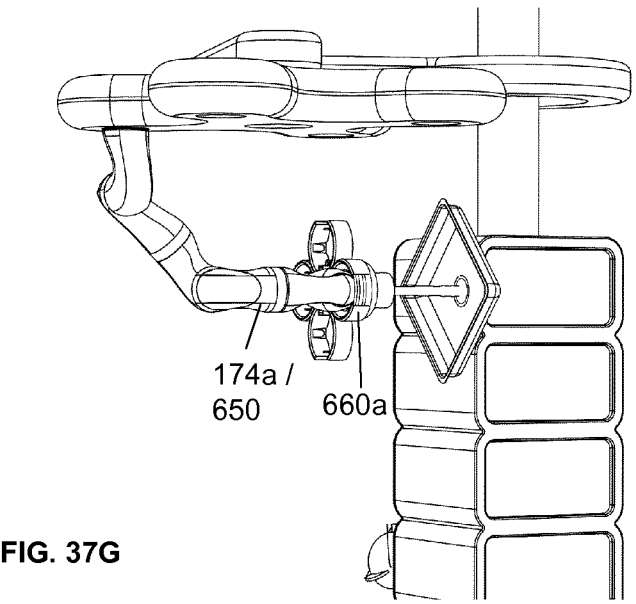

In FIGS. 37F and 37G, the robotic arm (174a/650) advances through the passage of the longitudinal sleeve, thereby unfolding it and drawing it over the robotic arm (174a/650). In FIG. 37F the robotic arm first fixes to three interface elements (638a-c) disposed in the longitudinal sleeve (622) that will couple with three actuators of the tool. The interface elements are visible in FIG. 37H.

Figure 37H:
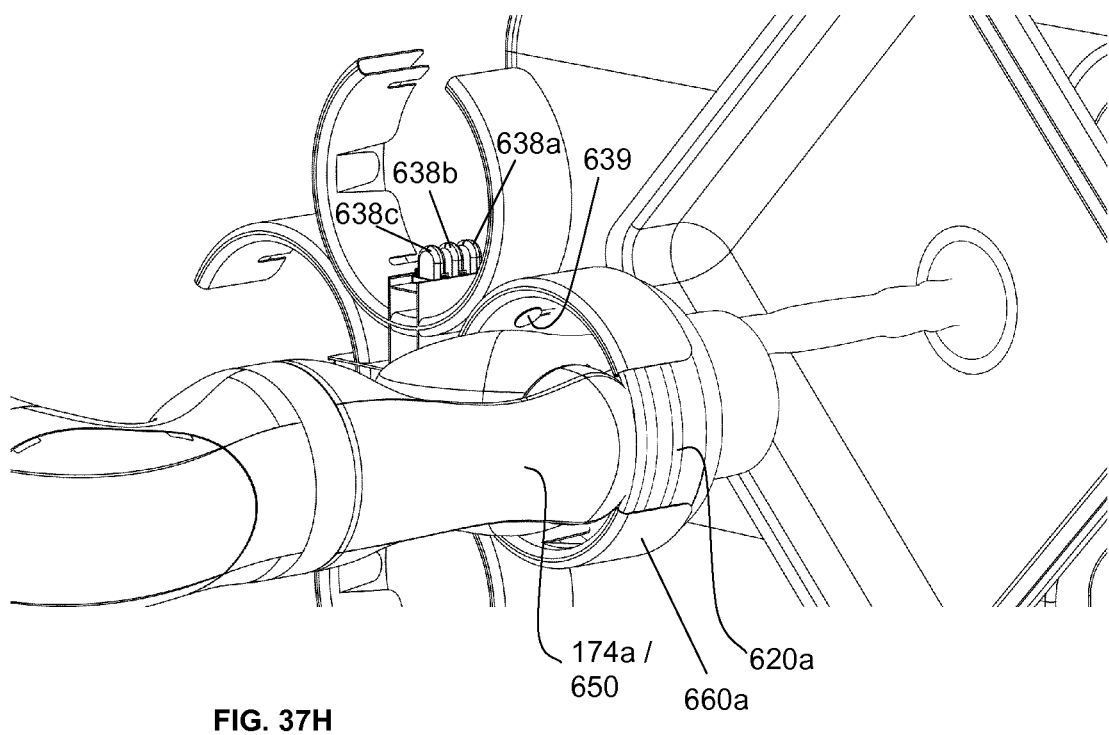

In FIG. 37H shows a detail of a robotic arm effector end travelling through one of the applicators (660a) and connected longitudinal sleeves/sterile drape (620a). The aforementioned interface elements (638a-c) are visible. A metal disc (639) attached to the sleeve (622) is provided for magnetic attachment to the robotic arm.

A fifth aspect relates to a tool for attachment to and for control by a robotic arm, the tool having a proximal and distal end. The proximal end is attachable to the robotic arm via a connector disposed at a proximal end of the tool and a complementary fitting on the robotic arm that grips the connector. The tool is provided with one or more slidable actuateable elements (SAE). The SAE may be a pull wire (e.g. FIG. 42A and B, 826) provided within a shaft of the tool for control of a distal end effector such as a gripper or scissor. The SAE may be a deployable motion restrictor (460) as described herein. The fifth aspect relates to a tool radial actuation assembly (TRAA) (820) (see for instance, FIGS. 40 to 42B, 44) disposed in the connector (820) of the tool, configured to a receive a radial force, provided by a fitting (860) on the robotic arm and to transform it to a longitudinal force for actuation of the SAE (826).

The TRAA (820) comprises one or more wedge-shaped bodies (822) radially slidable with respect to a central axis (A-A') of the connector (820). The wedge-shape body (822) is in contact with a longitudinally slidable body (824). The longitudinally slidable body preferably slides along central axis (A-A') of the connector. Radial movement of the wedge-shape body (822) inwards induces a longitudinal displacement of the longitudinally slidable body (824) (see for instance FIGS. 42A cf 42B). FIG. 44 panels A to C show step wise movement of the longitudinally slidable body (824) in a proximal (814) direction responsive to inwards radial actuation of the wedge-shaped bodies (822).

Preferably, there is a plurality of wedge-shaped bodies (822), arranged to form an annulus shape. The longitudinally slidable body (824) may be attached to compliant member (826) configured to bias the longitudinally slidable body (824) in a neutral position when no external force is applied to the wedge shape body (822). The application of a force to the wedge-shape body (822) displaces the longitudinally slidable body from the neutral position, and with release of the force the longitudinally slidable body returns to the neutral position.

The direction of the wedge determines the direction of displacement of longitudinally slidable body (844). Where a sloping edge of the wedge faces a proximal direction (812) (see for instance FIGS. 42A, B and FIGS. 44A to C), application of an external radial force moves the longitudinally slidable body (824) in a proximal direction. Where a sloping edge of the wedge faces a distal direction (814), application of an external radial force moves the longitudinally slidable body in a distal direction.

There may be a plurality of TRAAs, separated longitudinally along the connector. Each TRAA of the plurality may actuate a different SAE e.g. an end effector, and a deployable motion restrictor (460).

The fitting (860) on the effector end of the robotic arm may be provided with a fitting radial actuation assembly (FRAA) (862) (see for instance, FIGS. 41, 44) disposed in the fitting (860) of the robotic arm configured to provide a radial force for actuation TRAA on the tool (810). The FRAA (862) may comprise rotatable member (864) disposed with a cammed or eccentric surface (886), whereby rotation of the rotatable member (864) causes displacement of a slider (868) disposed in contact with the cammed or eccentric surface (886) (see for instance, FIGS. 43A, B and 44A, B). This slider may be configured such that it can move only in one DOF, preferably in a radial direction. The slider acts as an intermediate between the rotatable member and the TRAA. The function of the slider is to convert a rotational movement of the rotatable member into a radial movement. Restriction to a radial movement or perpendicular force avoids a tangential force component which might cause wrinkling or tearing. The cammed or eccentric surface (886) may be provided on an inside edge of the rotatable member (864). In FIG. 43B, the slider (868) is disposed at an open (O) position, while rotation of the rotatable member (864) moves the slider (868) to a closed (C) position in FIG. 44B. There may be a plurality of FRAAs (862a,b) separated longitudinally along the fitting (860). Each FRAA (862a,b) of the plurality may actuate a different TRAA (820a,b) of the tool (810).

The arrangement of TRAAs allows and co-operating TRAAs allows actuation of the tool though a sterile drape (620) (see for instance FIG. 45) without the requirement for interface element described elsewhere herein. The flexibility of the material of the sterile drape allows it to pass between the TRAA and the FRAA.

The fitting (860) at a distal end (814) may be disposed with a plurality of motion restrictors (870), configured to deploy radially (870') over the bendable proximal part (420) and to apply radial force the shaft region (430) to restrict bending of a straightened bendable proximal part (420), and/or to straighten a bend bendable proximal part (420). The motion restrictor may be a type of fitting radial actuation assembly (FRAA).

The sterile drape (620) may be configured so it provides an electric interface connection through the sterile barrier to connect an electronic socket in the robot arm to the sterile plug in the removable instrument. This connection may provide 1 or more isolated connections. These different connections can be organised as individual pins, concentric conductive rings, or segments (for example like segments of a pie)

The base of the fitting can be provided with a magnet. This magnet may be enabled and disabled. This magnet may be an electromagnet or a permanent magnet that can be reoriented to change the direction of the magnetic field. (like the magnet in a magnetic stand can be turned on and off).

The drape may be provided with an electrical conductive zone that fits in the base of the robot fitting. This electrical drape conductive zone is magnetically permeable (aluminium, . . . ) or ferromagnetic (iron, ferromagnetic stainless steel). When the conductive zone is in close proximity to the actuated fitting magnet, the drape conductive zone is pulled onto the magnet. This way the drape ensured to fit well into the fitting, as well as ensuring the electrical contact between the fitting magnet and the drape conductive zone.

The TRAA may be fitted with an electrical socket that matches an of the electrical conductive zone of the drape and an electrical socket of the robot fitting.

The TRAA may also fitted with a magnet or ferromagnetic material. When a magnet in the robot fitting is actuated, the TRAA is attracted into the robot socket onto the fitting magnet, with the electrical conductive zone in the drape in between. This ensures a consistent end stop during tool change. The magnetic force between the TRAA and the robot fitting also ensures good electrical contact.

When the TRAA includes a magnet, the magnet in the robot fitting may be made to reverse polarity. When the magnetic field of the robot fitting has a distal pole (e.g. north) that is inverse to the proximal pole in the TRAA (e.g. south), the TRAA attracts into the robot fitting.

When the distal robot fitting has the same pole as the proximal pole of the TRAA, the TRAA receives a magnetic force to eject it from the robot fitting.

Whatever distal pole (N or S) is being actuated in the robot fitting, the ferromagnetic conductive zone in the drape is always attracted to this pole.

When the magnetic field of the robot fitting magnet is turned off or is reoriented 90°, magnetic force to the ferromagnetic conductive zone in the drape is zero, and the drape may be removed (e.g. at the end of the surgical procedure).

The magnetic strength of the of the magnet in the TRAA should be smaller or equal to the magnetic strength of the magnet in the robot fitting. This to ensure that the magnetic force between the ferromagnetic conductive zone in the drape and the TRAA is always lower than the magnetic force between the ferromagnetic conductive zone in the drape and the robot fitting. This prevents that the drape is pulled out when the TRAA is removed during toolchange.

The invention claimed is:

1. A structural support unit, SSU, for vertical fitting in a room and for support of a boom unit comprising:
   a telescopic vertical supporting part, VSP, having an lower end and an upper end, the lower end configured for contacting a floor of the room and the upper end configured for attachment to a VSP receivable mounting in the ceiling of the room thereby stabilizing the structural support unit in relation to the room for support of the boom unit,
   wherein the boom unit is slidably and optionally revolutely attached to at least part of the VSP, a load of the boom unit comprises an assembly of two or more surgical robotic arms, the VSP comprises a telescopic part configured to retract and deploy the upper end (40) of the VSP, and the VSP receivable mounting comprises a slot into which the VSP upper end engages to stabilize the VSP in a vertical direction.

2. The structural support unit according to claim 1, wherein:

the base end of the VSP is configured for non-adjustable attachment to the floor and/or the upper end of the VSP is configured for non-adjustable attachment to the ceiling, or the base end of the VSP is configured for adjustable attachment to the floor and/or the upper end of the VSP is configured for adjustable attachment to the ceiling.

3. The structural support unit according to claim 1, wherein:

the base end of the VSP is disposed with a steerable dolly configured to support and transport the VSP, and to provide portability to the structural support unit.

4. The structural support unit according to claim 1, wherein the VSP comprises a load-bearing cylindrical tube, or a telescopic load-bearing cylindrical tube.

5. The structural support unit according to claim 1, wherein cables and tubing are disposed within void spaces of the VSP and/or the boom unit and/or a further boom unit.

6. The structural support unit according to claim 1, configured for use in an operating theater, wherein:

the VSP comprises a combination of a telescopic or non-telescopic load-bearing cylindrical tube and a load bearing or no-load-bearing storage unit configured to store one or more of:

a surgeon console for manual operation of the one or more surgical robotic arms, a light source, a high frequency coagulator, and an insufflator.

7. The structural support unit according to claim 1, wherein the slot has a circular profile.

8. A structural support unit for use as a vertical fitting in a room and for support of a boom unit in an operating theater, wherein the structural support unit comprises:

a telescopic vertical supporting part, VSP, having an lower end and an upper end, the lower end configured for contacting a floor of the room and the upper end configured for attachment to a VSP receivable mounting in the ceiling of the room thereby stabilizing the structural support unit in relation to the room for support of the boom unit, wherein:

the boom unit is slidably and optionally revolutely attached to at least part of the VSP, a load of the boom unit comprises an assembly of two or more surgical robotic arms, and the VSP comprises a telescopic part configured to retract and deploy the upper end of the VSP; and wherein the use comprises attaching the VSP upper end to the VSP receivable mounting placed in the ceiling of the operating theater.

9. The structural support unit according to claim 8, wherein:

the base end of the VSP is configured for non-adjustable attachment to the floor and/or the upper end of the VSP is configured for non-adjustable attachment to the ceiling, or the base end of the VSP is configured for adjustable attachment to the floor and/or the upper end of the VSP is configured for adjustable attachment to the ceiling.

10. The structural support unit according to claim 8, wherein:

the base end of the VSP is disposed with a steerable dolly configured to support and transport the VSP, and to provide portability to the structural support unit.

11. The structural support unit according to claim 8, wherein the VSP comprises a load-bearing cylindrical tube, or a telescopic load-bearing cylindrical tube.

12. The structural support unit according to claim 8, wherein the VSP receivable mounting comprises a slot into which the VSP upper end engages to stabilize the VSP in a vertical direction.

13. The structural support unit according to claim 8, wherein the slot has a circular profile.

14. The structural support unit according to claim 8, wherein cables and tubing are disposed within void spaces of the VSP and/or the boom unit and/or a further boom unit.

* * * * *